(12) United States Patent
Lau et al.

(10) Patent No.: US 8,945,509 B2
(45) Date of Patent: Feb. 3, 2015

(54) MAGNETIC BEADS HAVING SURFACE GLYCOCONJUGATES AND USE THEREOF

(75) Inventors: Aldrich Lau, Palo Alto, CA (US); Robert Eason, Los Gatos, CA (US); Maxim Brevnov, Union City, CA (US); Handong Li, San Jose, CA (US); Kevin Hacker, Cupertino, CA (US)

(73) Assignee: Life Technologies Corporation, Carlsbad, CA (US)

( * ) Notice: Subject to any disclaimer, the term of this patent is extended or adjusted under 35 U.S.C. 154(b) by 314 days.

(21) Appl. No.: 13/215,157

(22) Filed: Aug. 22, 2011

(65) Prior Publication Data

US 2012/0045767 A1 Feb. 23, 2012

Related U.S. Application Data

(60) Provisional application No. 61/375,320, filed on Aug. 20, 2010.

(51) Int. Cl.
*A61K 51/00* (2006.01)
*A61B 5/055* (2006.01)
*C12Q 1/70* (2006.01)

(52) U.S. Cl.
USPC ............................ 424/1.73; 424/9.323; 435/5

(58) Field of Classification Search
USPC .................................. 424/9.323, 1.73; 435/5
See application file for complete search history.

(56) References Cited

U.S. PATENT DOCUMENTS

| 4,001,197 A | | 1/1977 | Mitchell et al. |
| 5,858,534 A | * | 1/1999 | Sucholeiki ................... 428/407 |
| 7,560,228 B2 | | 7/2009 | Rudi et al. |
| 2005/0271553 A1 | | 12/2005 | Ramstad et al. |
| 2006/0051583 A1 | | 3/2006 | Lau et al. |
| 2006/0160122 A1 | | 7/2006 | Harrold et al. |
| 2009/0186346 A1 | | 7/2009 | D'Auriac |

OTHER PUBLICATIONS

Boseggia et al., "Toward Efficient Zn(II)-Based Artificial Nucleases", *Journal of the American Chemical Society*, vol. 126, Issue 14, Apr. 14, 2004, 4543-4549.
Cheng et al., "Synthesis and Enzyme-Specific Activation of Carbohydrate-Geldanamycin Conjugates with Potent Anticancer Activity", *Journal of Medicinal Chemistry*, vol. 48, Issue 2, Jan. 27, 2005, 645-652.
Eberhardt et al., "Synthesis of pentafluorophenyl(meth)acrylate polymers: New precursor polymers for the synthesis of multifunctional materials", *European Polymer Journal*, vol. 41, Issue 7, Jul. 2005, 1569-1575.
Lis et al., "Lectins: Carbohydrate-Specific Proteins That Mediate Cellular Recognition", *Chemical Reviews*, vol. 98, Issue 2, Apr. 2, 1998, 637-674.
Mammen et al., "Polyvalent Interactions in Biological Systems: Implications for Design and Use of Multivalent Ligands and Inhibitors", *Angewandte Chemie*, vol. 37, Issue 20, Nov. 2, 1998, 2754-2794.

(Continued)

*Primary Examiner* — Jezia Riley

(57) ABSTRACT

Magnetic beads that include polyvalent ligands comprising various carbohydrates are described. Methods for fabricating such magnetic beads are also provided as well as methods of their use to capture and enrich pathogen cell population for subsequent culture, lysis and identification.

33 Claims, 5 Drawing Sheets

(56) References Cited

OTHER PUBLICATIONS

McCain et al., "Inversion-independent phase variation of type 1 fimbriae in *Escherichia coli*.", *Journal of Bacteriology*, vol. 175, Issue 14, Jul. 1993, 4335-4344.

Sokurenko et al., "Diversity of the *Escherichia coli* Type 1 Fimbrial Lectin", *The Journal of Biological Chemistry*, vol. 272, No. 28, Jul. 11, 1997, 17880-17886.

Tarasenko et al., "Glycoconjugates for the recognition of *Bacillus* spores", *Carbohydrate Research*, vol. 339, Issue 18, Dec. 27, 2004, 2859-2870.

Satoh, et al., "Immobilization of Saccharides and Peptides on 96-Well Microtiter Plates Coated with Methly Vinyl Ether-Maleic Anhydride Copolymer", *Analytical Biochemistry*, vol. 260, No. 1, Jun. 15, 1998, 96-102.

Sun, et al., "Site-Specific Mutlivalent Carbohydrate Labeling of Quantum Dots and Magnetic Beads", *ChemBioChem*, vol. 5, No. 11, Nov. 5, 2004, 1593-1596.

Sun, et al., "The Hydroxyl-Functionalized Magnetic Particles for Purification of Glycan-Binding Patterns", *Current Pharmaceutical Biotechnology*, vol. 10, No. 8, Dec. 2009, 753-760.

* cited by examiner

MAGNETIC BEADS HAVING SURFACE GLYCOCONJUGATES AND USE THEREOF

CROSS REFERENCE TO RELATED APPLICATION

This patent application claims priority under 35 U.S.C. §119(e) to U.S. Provisional patent application, U.S. Ser. No. 61/375,320, filed Aug. 20, 2010, the entire contents of which are incorporated herein by reference.

FIELD OF THE DISCLOSURE

This disclosure relates generally to compositions, systems and methods for detecting biological target analytes (such as microorganisms including bacteria, fungi and viruses) in a sample. More specifically, this disclosure relates to magnetic beads having surface glycoconjugates, methods of making such beads and to methods of use thereof to capture microorganism(s) (such as bacteria, fungi, viruses) from samples for detection and identification.

BACKGROUND

Food companies are required to test for presence of common food pathogens such as *E. coli* 0157:H7, *Listeria*, *Salmonella*, *Campylobacter*, *Vibrio*, etc. to protecting public health. Tests for detecting food pathogens are also performed by health service labs and government agencies to monitor and track outbreaks of food poisoning. Reducing the time necessary to obtain results of food testing is important for the food processing industry as it reduces the time and costs associated with storage of food prior to delivery till food testing results are obtained.

The most common method for identifying the presence of microorganisms is by enriching in selective broths and platting on defined agars. Classical platting methods require 3-5 days for confirmation (sometimes longer depending on the organism), and advanced skills in microbiology. The largest unmet need within the food testing market is the ability to produce results in one work shift, which is typically defined as eight hours or less.

Molecular methods such as PCR currently play a small role in testing presence of microorganisms. Real-time PCR is valuable because it combines simplicity with specificity and sensitivity. PCR, however, has its limitations, due to the necessity of sample preparation which can be time-consuming, and is technically challenging and expensive in view of the existence of a wide variety of food samples having different chemical and physical properties, and the necessity to process very large sample volumes. In addition many foods, such as meat products, contain PCR inhibitors.

One solution for this problem relies on magnetic properties. For example, magnetic seeds (magnetite) were used to capture single cell organisms in the presence of a calcium chloride binder, as described in U.S. Pat. No. 4,001,197. The magnetic beads can be DYNABEADS (Dynal AS, Oslo, Norway) functionalized to have positively or negatively charged, hydrophilic or hydrophobic surfaces, as taught in U.S. Pat. No. 7,560,228. Pathogen cells can also be captured by non-specific adsorption on the surfaces of magnetic beads (BUGS'n BEADS™ from NorDiag Inc., West Chester, Pa., US).

The above mentioned techniques rely on non-specific adsorption that may also bind various types of proteins that can inhibit and/or interfere with subsequent PCR reactions. The inhibition/interference can be exacerbated by subsequent in situ lysis and PCR in the presence of these proteins-bound magnetic beads.

Bacterial cellular surfaces comprise a variety of complex carbohydrate structures, such as glycoproteins, glycolipids, glycosaminoglycans, and proteoglycans. These glycoconjugates play a central role in cell-to-cell adhesion and subsequent recognition and receptor activation, as discussed in G. M. Whitesides et al., *Angew. Chem. Int. Ed.* 1998, 37, 2754-2794. And yet, the surfaces of different bacterial species are chemically and morphologically quite distinct.

Certain cells are able to selectively bind to one particular glycoconjugate but not the others. In practical applications, pathogen cells can be captured with magnetic beads having carbohydrates, including monosaccharides, disaccharides, oligosaccharides, and polysaccharides, immobilized on the bead surfaces, as described in the published U.S. Patent Application No. 2009/0186346A1. The binding of a pathogen cell onto a carbohydrate-modified magnetic bead is "monovalent" as schematically shown on FIG. 1.

The affinity, efficiency and binding strength of the structure depicted on FIG. 1 are weak. It may not withstand repetitive washing and rinsing to remove of debris and undesirable materials from the biological sample. Accordingly, better methods have to be employed to allow those skilled in the art to solve one or more of the above-mentioned problems.

SUMMARY OF DISCLOSURE

The present application, in some embodiments, describes compositions operable for "polyvalent" binding to cells—such as, but not limited to, cells of microorganisms (including bacteria, fungi and viruses); methods of synthesizing these compositions and methods of using compositions of the disclosure to detect cells present in a sample. In some embodiments, compositions of the disclosure may be used in methods for food testing for rapid, robust and cost-effective capture and subsequent analysis of microorganisms present in food samples.

In some embodiments, the present disclosure describes compositions, comprising: a paramagnetic bead; a plurality of hydrophilic copolymer bridges, each bridge being covalently bonded to the paramagnetic bead; and a plurality of carbohydrates, each carbohydrate being covalently bonded to the same or different hydrophilic copolymer bridge by forming a glycoconjugate with the respective hydrophilic copolymer.

In some embodiments, compositions of the disclosure may have the structure:

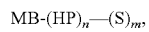

wherein MB is a magnetic bead; HP is hydrophilic polymer bridge; S is a carbohydrate; and each of n and m is an integer, and wherein n≥1 and m≥1, with the further proviso that if n=1, then m≥2.

In some embodiments, a composition of the disclosure may have each hydrophilic polymer bridge (HP) bonded to a paramagnetic bead (MB) via a link formed by an amino group. In some embodiments a paramagnetic bead (MB) may be a bead described by DYNABEADS®.

In some embodiments, each hydrophilic copolymer may be the same in a composition of the disclosure. In some embodiments, at least one hydrophilic copolymer is different from at least one other hydrophilic copolymer, in a composition of the disclosure.

In some embodiments, hydrophilic copolymer bridges are formed of functionalized hydrophilic copolymers and may be functionalized acrylates, poly(alkylene glycols), alkoxy poly (alkylene glycols), copolymers of methylvinyl ether and maleic acid, urethanes, ethyleneimines, polyurethane-polyether copolymers, copolymers having units derived from vinyl alcohol, N-vinyl lactams, vinyl pyrrolidone, amides, maleic anhydride, styrenesulfonates, vinylsulfonic acid, vinylsulfonates, N-vinylamides or 3-hydroxybutyric acid, and various combinations and derivatives thereof.

In some embodiments, a composition of the disclosure may comprise functionalized acrylates such as but not limited to functionalized copolymers having units derived from acrylic acid, methacrylic acid, 2-hydroxyalkyl acrylate, 2-hydroxyalkylmethacrylate, acrylamides, methacrylamides, epoxyacrylates, and combinations and derivatives thereof.

In some embodiments, each of the functionalized hydrophilic copolymers, in a composition of the disclosure, may comprise a plurality of functional groups, comprising: a first functional group to form a covalent linkage between a magnetic bead and a respective hydrophilic copolymer bridge; and at least one second functional group, to attach at least one carbohydrate to the hydrophilic copolymer by forming glycoconjugate(s) between the carbohydrate(s) and the hydrophilic copolymer. In some embodiments, the first functional group and the second functional group may be the same functional group. In some embodiments, in a plurality of functional groups at least one functional group is different from at least one other functional group. Exemplary non limiting functional groups may include without limitation: an amino, a hydroxyl, a carboxyl, a N-hydroxysuccinimide, an ester of pentafluorophenol, a maleimide, an epoxy, an aldehyde, a ketone, a cyanuryl, a pyrrolidinedione, an alkyne and/or an azide and/or combinations of these groups.

In some embodiments, a composition of the disclosure may comprise carbohydrates comprising monosaccharides, disaccharides, trisaccharides, tetrasaccharides, oligosaccahrides, polysaccarides or N-modified derivatives thereof. In some exemplary embodiments, monosaccharides in a composition of the disclosure may be glucose, galactose, fructose, mannose, lyxose and xylose and/or N-modified derivatives thereof. In some exemplary embodiments, disaccharides in a composition of the disclosure may be sucrose, lactose, maltose, isomaltose, lactulose, trehalose and/or N-modified derivatives thereof. In some exemplary embodiments, polysaccharides in a composition of the disclosure may be cellulose, glycan, dextrin, amylase, amylopectine and/or N-modified derivatives thereof.

In some exemplary embodiments, carbohydrates in a composition of the disclosure may be a sialic acid, amine-containing saccharides, saccharide conjugates of glycans, saccharide conjugates of aminocyclitols and/or N-modified derivatives thereof.

In some embodiments, a composition of the disclosure may comprise the same carbohydrate for each carbohydrate moiety. In some embodiments, at least one carbohydrate is different from at least one other carbohydrate, in a composition of the disclosure.

In some embodiments, a composition of the disclosure may comprise hydrophilic copolymers where each hydrophilic copolymer has the Hildebrand solubility parameter δ of at least about 10 MPa$^{1/2}$. In some embodiments, a composition of the disclosure may comprise hydrophilic copolymers wherein the Hildebrand solubility parameter δ is at least about 20 MPa$^{1/2}$.

In some embodiments, a composition of the disclosure may comprise hydrophilic copolymers wherein the Hildebrand solubility parameter δ is at least about 25 MPa$^{1/2}$.

In some embodiments, a composition of the disclosure may comprise hydrophilic copolymers each having the weight-averaged molecular weight of between about 5,000 and about 5,000,000 Daltons. In some embodiments, the weight-averaged molecular weight of hydrophilic copolymers in compositions of the disclosure may be between about 50,000 and about 1,000,000 Daltons. In some embodiments, the weight-averaged molecular weight of hydrophilic copolymers in compositions of the disclosure may be between about 100,000 and about 500,000 Daltons.

The disclosure also describes methods of making compositions of the disclosure. A method for fabricating a paramagnetic bead composition, may comprise: immobilizing a plurality of functionalized hydrophilic copolymers on the surface of a paramagnetic bead; and bonding at least one carbohydrate to each of at least two hydrophilic copolymers, wherein each of the functionalized hydrophilic copolymers includes a plurality of functional groups, comprising a first functional group and at least one second functional group, to thereby obtain the paramagnetic bead composition.

In some embodiments, the step of immobilizing comprises reacting a plurality of functionalized hydrophilic copolymers with a paramagnetic bead, wherein a covalent linkage is formed between the paramagnetic bead and each hydrophilic copolymer.

In some embodiments, the step of bonding comprises reacting a plurality of functionalized hydrophilic copolymers with at least one carbohydrate(s), wherein at least two glycoconjugates are formed between the at least one carbohydrate and the hydrophilic copolymers. In some embodiments of a method of the disclosure, hydrophilic copolymers may be functionalized and in non-limiting examples may comprise: functionalized acrylates, poly(alkylene glycols), alkoxy poly (alkylene glycols), copolymers of methylvinyl ether and maleic acid, urethanes, ethyleneimines, polyurethane-polyether copolymers, and copolymers having units derived from vinyl alcohol, N-vinyl lactams, vinyl pyrrolidone, amides, maleic anhydride, styrenesulfonates, vinylsulfonic acid, vinylsulfonates or 3-hydroxybutyric acid, and/or derivatives thereof.

In some example embodiments, functionalized acrylates may comprise functionalized copolymers having units derived from acrylic acid, methacrylic acid, 2-hydroxyalkyl acrylate, 2-hydroxyalkylmethacrylate, acrylamides, methacrylamides, epoxy-acrylates, and/or derivatives thereof.

In some embodiments, in the step of immobilizing may comprising reacting a plurality of functionalized hydrophilic copolymers with a paramagnetic bead, wherein a covalent linkage is formed between the paramagnetic bead and each hydrophilic copolymer, wherein the plurality of functional groups comprises the same functional group(s).

In some embodiments of the method, in the plurality of functional groups at least one functional group is different from at least one other functional group.

In some embodiments, a functional group may be a hydroxyl, a carboxyl, a N-hydroxysuccinimide (NHS), an epoxy, a cyanuryl, an alkyne and a pyrrolidinedione group.

Methods of the disclosure, in some embodiments, may use carbohydrates comprising monosaccharides, disaccharides, trisaccharides, tetrasaccharides, oligosaccharides, polysaccharides and/or N-modified derivatives thereof.

Exemplary monosaccharides used may comprise glucose, galactose, fructose, mannose, lyxose and xylose and/or N-modified derivatives thereof. Exemplary disaccharides used may comprise sucrose, lactose, maltose, isomaltose, lactulose, trehalose and/or N-modified derivatives thereof. Exemplary polysaccharides used in methods of the disclosure may comprise cellulose, glycan, dextrin, amylase, amylopectine and N-modified derivatives thereof.

In some embodiments, methods of the disclosure may use carbohydrates such as, but not limited to, sialic acid, amine-containing saccharides, saccharide conjugates of glycans, saccharide conjugates of aminocyclitols and/or N-modified derivatives thereof.

In some embodiments, a method of making a composition of the disclosure may comprise using carbohydrates wherein at least two carbohydrates are bonded and each individual carbohydrate is the same. In some embodiments of a method of the disclosure, at least two carbohydrates are bonded and at least one individual carbohydrate is different from at least one other individual carbohydrate.

The present disclosure also describes methods for capturing a population of microorganisms from a biological sample, comprising: combining a composition of the disclosure comprising: a paramagnetic bead; a plurality of hydrophilic copolymer bridges, each bridge being covalently bonded to the paramagnetic bead; and a plurality of carbohydrates, each carbohydrate being covalently bonded to the same or different hydrophilic copolymer bridge by forming a glycoconjugate with the respective hydrophilic copolymer, with the biological sample for a time to form composition-microorganism complexes; separating the composition-microorganism complexes from the sample under a magnetic field; and collecting the captured microorganisms, wherein the population of microorganisms has binding specificity for the carbohydrate.

A variety of microorganisms may be detected and/or captured using compositions of the disclosure such as bacteria including gram negative and gram positive species; viruses, fungi, and spores thereof.

In some embodiments of the method of capturing microorganisms, the population of microorganisms captured is a subpopulation of microorganisms present in the biological sample.

In some embodiments of the method, the carbohydrate is mannose and the population of microorganisms has binding specificity for mannose.

A method of capturing microorganisms of the disclosure may additionally comprising downstream steps for detection and identification of the microbe. Such steps in non-limiting examples may comprise one or more of the following steps: performing a nucleic acid extraction on the captured microorganisms; Real-Time PCR analysis, culturing the captured microorganisms to increase the number of microorganisms for further analysis, DNA sequencing, immunoassays and the like.

These and other features of the present disclosure will become better understood with reference to the following description, drawings, and appended claims.

BRIEF DESCRIPTION OF THE DRAWINGS

The drawings described below, are for illustration purposes only, and are not intended to limit the scope of the present disclosure in any way.

DETAILED DESCRIPTION OF THE EMBODIMENTS

Figure 1:
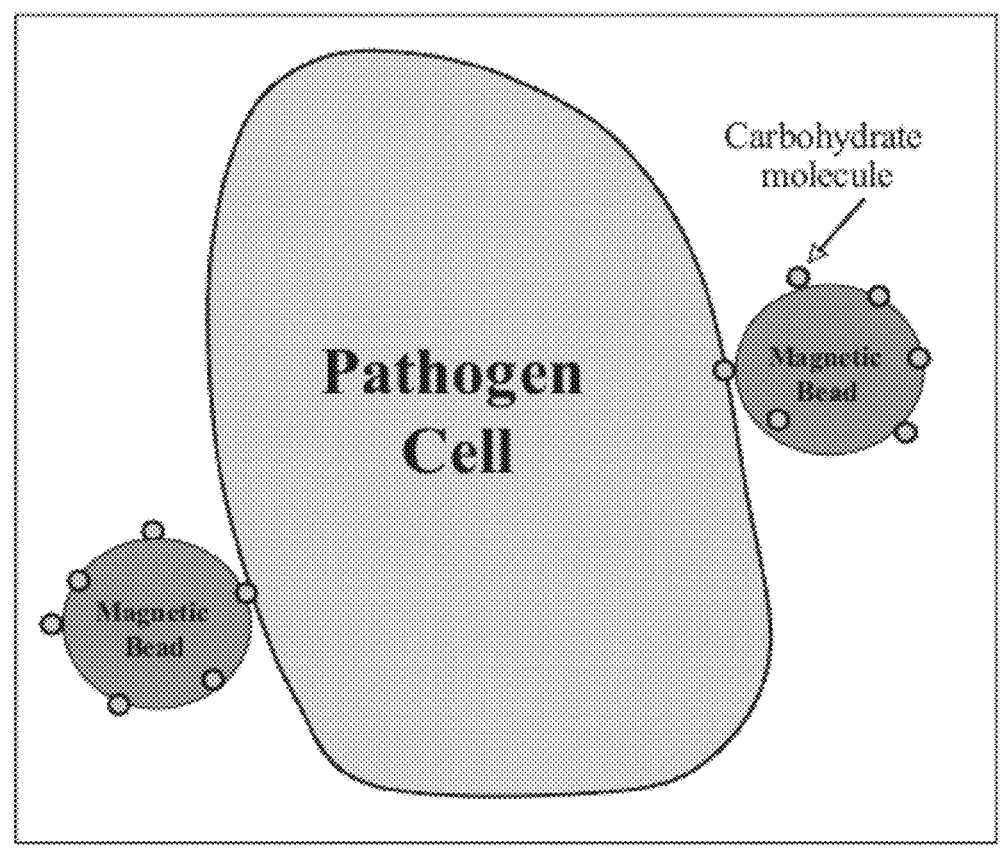
FIG. 1 depicts a scheme showing monovalent interactions between a pathogen cell and a carbohydrate-modified magnetic bead.

Reference will now be made in detail to some embodiments of the disclosure. While the disclosure will be described in conjunction with the embodiments discussed below, it will be understood that they are not intended to limit the disclosure to those embodiments. On the contrary, the disclosure is intended to cover alternatives, modifications, and equivalents, which may be included within the disclosure as defined by the appended claims.

The present disclosure relates to compositions comprising magnetic beads that include "polyvalent" ligands comprising a plurality of carbohydrates that are operable to capture cell populations in samples (such as microorganism cells) using polyvalent ligand binding. Compositions of the disclosure, methods for making such compositions and methods of using the present compositions for capturing and/or detecting cells and microbes (such as bacterial cells, viruses and fungi) are described.

According to some embodiments of the disclosure, magnetic bead compositions are provided, which comprise a paramagnetic bead, a plurality of hydrophilic copolymer bridges, each bridge being covalently bonded to the paramagnetic bead, and a plurality of carbohydrates, each carbohydrate being connected to the same or different hydrophilic copolymer by forming a glycoconjugate with the respective hydrophilic copolymer.

According to other embodiments of the disclosure, methods for fabricating paramagnetic bead compositions are provided. Such methods include immobilizing a plurality of functionalized hydrophilic copolymers on the surface of a paramagnetic bead and bonding at least one carbohydrate to the hydrophilic polymer, wherein each of the functionalized hydrophilic copolymers includes a plurality of functional groups, comprising a first functional group and at least one second functional group.

According to yet other embodiments of the disclosure, methods of using polyvalent magnetic beads for capturing a microorganism from a biological sample are provided. Such methods include combining a paramagnetic bead composition of the disclosure with a biological sample for a certain time to form a composition-microorganism complex, removing the composition-microorganism complex under a magnetic field, and collecting the captured microorganism, where a paramagnetic bead composition of the disclosure includes a paramagnetic bead, a plurality of hydrophilic copolymer bridges, each bridge being covalently bonded to the paramagnetic bead, and a plurality of carbohydrates, each carbohydrate being connected to the same or different hydrophilic copolymer by forming a glycoconjugate with the respective hydrophilic copolymer. A method of the disclosure may further comprise analyzing a captured microorganism by one or more methods for microorganism and viral analysis such as but not limited to, nucleic acid extraction, DNA extraction, amplification of nucleic acids (e.g., Real-Time PCR and/or TaqMan® Assay), hybridization of nucleic acids, DNA sequencing and the like. For example, in one embodiment a method may further comprises performing a nucleic acid extraction and Real-Time PCR analysis of the captured microorganisms. In further embodiments, the method comprises culturing the captured microorganisms for further analysis.

In other embodiments, a method for capturing a population of microorganisms from a biological sample is provided comprising combining a composition of the disclosure with a biological sample for a time to form composition-microorganism complexes; separating the composition-microorganism complexes from the sample under a magnetic field; and collecting the captured microorganisms, wherein the population of microorganisms has binding specificity for the carbohydrate comprised in the composition of the disclosure. In some embodiments, the population of microorganisms captured may be a subpopulation of microorganisms of the total population of microorganisms present in a biological sample.

In one embodiment, a carbohydrate moiety comprised in a composition of the disclosure is mannose and the population of microorganisms captured by a method of the disclosure, using the composition comprising mannose, has binding specificity for mannose.

Unless stated otherwise, the following terms, definitions, and abbreviations as used herein are intended to have the following meanings. Whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended.

For the purposes of the present disclosure, the term "glycoconjugate" refers to a carbohydrate (such as a saccharide) covalently linked to another chemical group, e.g., to a polymer. Glycoconjugates contain glycosidic linkages, e.g., glycolipids, glycopeptides, glucoproteins or glycosaminoglycans and sialosides.

The term "saccharide" as used herein refers to any molecule comprising a saccharide moiety and encompasses both monosaccharides and polysaccarides such as di-, tri-, tetra-, oligo-saccharides, etc. "Saccharide" may also be used to refer to biomolecules containing saccharides, among other moieties. The term "polyvalent glycoconjugate" as used herein refers to glycoconjugates comprising a plurality of carbohydrates covalently linked to another chemical group.

The term "monosaccharide" as used herein refers to any carbohydrate ("a simple sugar"), such as triose, tetrose, pentose or hexose (including both aldose and ketose forms) that cannot be hydrolyzed to form simpler sugars.

The term "polysaccharide" as used herein refers to polymers made up of a plurality of monosaccharide units joined together by glycosidic linkages.

The term "oligosaccharide" as used herein refers to a polysaccharide containing a small number (e.g., three to ten) of saccharide units.

The term "glycoprotein" as used herein refers to a biological molecule comprising a protein and a carbohydrate covalently linked together.

The term "glycosidic linkage" as used herein refers to a bond formed between the hemiacetal group of a saccharide, or of a derivative thereof, and the hydroxyl group of an organic compound, e.g., of an alcohol or a glycol.

The terms "magnetic bead" and "magnetic particle" as used herein refer to any bead or other solid particulate material, which can be spherical or irregularly shaped, and which can be attracted by a magnetic field. As used herein, the meanings of the terms "magnetic bead" and "magnetic particle" are identical and they are used interchangeably.

The term "magnetic" for the purposes of the present disclosure means "paramagnetic." The term "paramagnetic" as used herein refers to a material that is not magnetic naturally (i.e., not magnetic in the absence of the externally applied magnetic field), but when placed in such an externally applied magnetic field, is magnetized to form its own magnetic field, which is parallel to the applied field, to the extent proportional to the applied field.

The term "polyvalent" for the purposes of the present disclosure means "multifunctional" and, accordingly, "polyvalent magnetic bead" refers to a magnetic bead bearing at least one scaffold comprising a hydrophilic polymer having at least two carbohydrates pendant from the hydrophilic polymer's chain, or at least two scaffolds each comprising a hydrophilic polymer having at least one carbohydrate(s) pendant from the hydrophilic polymers' chains.

The term "monomer," in accordance with the definition adopted by the International Union of Pure and Applied Chemistry (IUPAC), refers to a molecule which is capable of undergoing polymerization thereby contributing constitutional units to the essential structure of a macromolecule (a polymer).

The term "polymer" is defined for the purposes of the present disclosure as being inclusive of copolymers and oligomers. The term "copolymer" is defined as a polymer derived from more than one species of monomer, including copolymers that are obtained by copolymerization of two monomer species, those obtained from three monomers species ("terpolymers"), those obtained from four monomers species ("quaterpolymers"), etc. The term "oligomer" is defined as a low molecular weight polymer in which the number of repeating units does not exceed twenty.

The term "copolymer" is further defined as being inclusive of random copolymers, alternating copolymers, graft copolymers, and block copolymers. The term "random copolymer" is defined as a copolymer comprising macromolecules in which the probability of finding a given monomeric unit at any given site in the chain is independent of the nature of the adjacent units. In a random copolymer, the sequence distribution of monomeric units follows Bernoullian statistics. The term "alternating copolymer" is defined as a copolymer comprising macromolecules that include two species of monomeric units in alternating sequence. Copolymers of any tacticity are included within the term "copolymer."

The term "hydrophilic polymer" is defined for the purposes of the present disclosure as a polymer, which has a range of water solubility at ambient conditions from water miscible, slightly water soluble, to water swellable.

The term "Hildebrand solubility parameter" is defined as a parameter indicating the cohesive energy density of a substance. The $\delta$ parameter is determined as $\delta=(\Delta E/V)^{1/2}$, wherein $\delta$ is Hildebrand solubility parameter, $\Delta E$ is the energy of vaporization, and V is the molar volume.

For the purposes of the present disclosure, "hydrophilic polymer" and "hydrophilic copolymer" are defined as the (co)polymers that exhibit Hildebrand solubility parameter $\delta$ that is equal to or greater than about 10 $MPa^{1/2}$ (for comparison purposes only, acetone exhibits $\delta=19.7$ $MPa^{1/2}$), such as equal to, or greater than, about 20 $MPa^{1/2}$, for example, equal to, or greater than about 25 $MPa^{1/2}$ (e.g., polyacrylamide and water exhibit $\delta$ of 27 and 48 $MPa^{1/2}$, respectively).

The terms "acrylic," "polyacrylic," "acrylate" or "polyacrylate" refer to a product that is inclusive of a monomer, oligomer, and pre-polymer, as applicable, having at least one acrylic moiety, $CH_2$=CH—COO—, or methacrylic moiety, CH₂=C(CH₃)—COO—, or derived from a product having at least one acrylic moiety or methacrylic moiety (e.g., polymer by polymerization of such a product).

The abbreviation "PCR" refers to polymerase chain reaction, which is a method of producing multiple copies of specific DNA sequences for detection and evaluation.

The abbreviation "TaqMan® PCR" refers to a kind of PCR that utilizes the 5'-3' nuclease activity of Taq polymerase to cleave a dual-labeled probe during hybridization to the complementary target sequence and fluorophore-based detection.

As used herein, the term "Ct" represents the PCR cycle number when the signal is first recorded as statistically significant. The term "Cq" designates quantification cycle and is interchangeable with the term "Ct" (See e.g., "MIQE: Minimum Information for Publication of Quantitative Real-Time PCR Experiments," *Clinical Chemistry* 55:4; 611-622 (2009)).

The use of "or" herein means "and/or" unless stated otherwise or where the use of "and/or" is clearly inappropriate. The use of "a" herein means "one or more" unless stated otherwise. The use of "comprise," "comprises," "comprising," "include," "includes" and "including" are interchangeable and not intended to be limiting. It should also be understood that in some embodiments the order of steps or order for performing certain actions is immaterial so long as the present teachings remain operable. Moreover, in some embodiments two or more steps or actions can be conducted simultaneously.

The present disclosure describes compositions having "polyvalent" ligand binding characteristics. Compositions of the disclosure comprise magnetic beads or magnetic particles and a plurality of hydrophilic polymers covalently bonded to such magnetic beads or particles. In some embodiments, compositions of the disclosure also comprise a plurality of carbohydrates, each carbohydrate being connected to the same or different hydrophilic copolymer by forming a glycoconjugate with the respective hydrophilic copolymer.

The covalent bonding of the hydrophilic polymers to the magnetic beads or magnetic particles is achieved by reaction of functional groups that are present on the surface of the magnetic beads or magnetic particles with the functional groups that are present in the hydrophilic polymers, as described in detail below. As a result of such a reaction, a covalent link is formed, which can be can be, for example, via an amide link or a secondary amine link, as described in more detail below. Those having ordinary skill in the art, in light of this specification, will realize that depending on the nature of the functional groups that are present on the surface of the beads and the nature of the functional groups that are present in the hydrophilic polymers, other types of covalent links may be formed via which the hydrophilic polymers can be covalently bonded to the magnetic beads or particles.

The magnetic beads or particles are made of a paramagnetic material and can be spherical or irregularly shaped. The spherical beads can have a diameter between about 0.1 μm and about 50 μm, such as between about 1 μm and about 5 μm. One type of magnetic beads that may be used is Dynabeads® available from Dynal AS, Oslo, Norway. Those having ordinary skill in the art, in light of this specification, can select other suitable magnetic beads. Some non-limiting examples of other suitable magnetic beads that may be used for the purpose of covalent binding of hydrophilic polymer(s) include MagMax™ beads available from Applied Biosystems, Foster City, Calif., BioMag® beads available from Polysciences, Inc. of Warrington, Pa. or BcMag™ beads available from BioClone Inc. of San Diego, Calif., so long as such beads are modified to contain the surface functional groups described below.

One embodiment of the disclosure describes magnetic bead compositions comprising a paramagnetic bead, a plurality of hydrophilic copolymer bridges, each bridge being covalently bonded to the paramagnetic bead, and a plurality of carbohydrates, each carbohydrate being connected to the same or different hydrophilic copolymer by forming a glycoconjugate with the respective hydrophilic copolymer. In some embodiments, a composition of the disclosure as described here may have "polyvalent" ligand binding characteristics. For example, poly(glycoconjugates) compositions of the disclosure may be operable to bind to one or more molecules on the surface of microorganisms, such as, but not limited to, bacteria, fungi, viruses and spores thereof. Accordingly, compositions of the disclosure may be used in methods of the disclosure (described in detail below) to capture, enrich and/or detect cell populations, such as microbial cell populations from samples that may contain/be contaminated with a microbe.

In some embodiments, hydrophilic polymers that are covalently attached to a magnetic bead may bear at least two carbohydrate residues pendant from at least one polymeric chain. A general structure of a composition of the disclosure can be schematically expressed as structure (A):

$$\text{MB-(HP)}_n\text{—(S)}_m, \quad (A)$$

wherein "MB" is a magnetic bead, "HP" is hydrophilic polymer, "S" is a carbohydrate (i.e., a sugar), n is an integer indicating the number of hydrophilic polymeric chains covalently bonded to the magnetic bead, and m is an integer indicating the number of carbohydrate residues conjugated to each hydrophilic polymer. Hydrophilic polymer(s) serve as bridge(s) connecting a magnetic bead with one or more carbohydrate(s). As discussed in more detail below, each hydrophilic polymer is covalently bonded to the magnetic bead through its pendant functional groups along the polymer chain (see FIG. 2), and is also connected to the carbohydrate portion by forming a glycoconjugate.

It should be understood that the number of hydrophilic polymeric chains covalently bonded to the magnetic bead is at least one and the number of carbohydrate residues conjugated to each hydrophilic polymer is also at least one. In other words, in Structure A above, n≥1 and m≥1; however, if n=1, then m≥2.

In some embodiments, the capability of the present compositions for capturing microorganisms relies on the number and chemical nature of carbohydrate molecules along a hydrophilic polymer chain. Those having ordinary skill in the art, in light of this disclosure, can appreciate the kinetic benefit of having a polyvalent interaction extending away from a magnetic bead/particle, and can determine the number of polymer chains that are to be attached to a magnetic bead.

Figure 2:
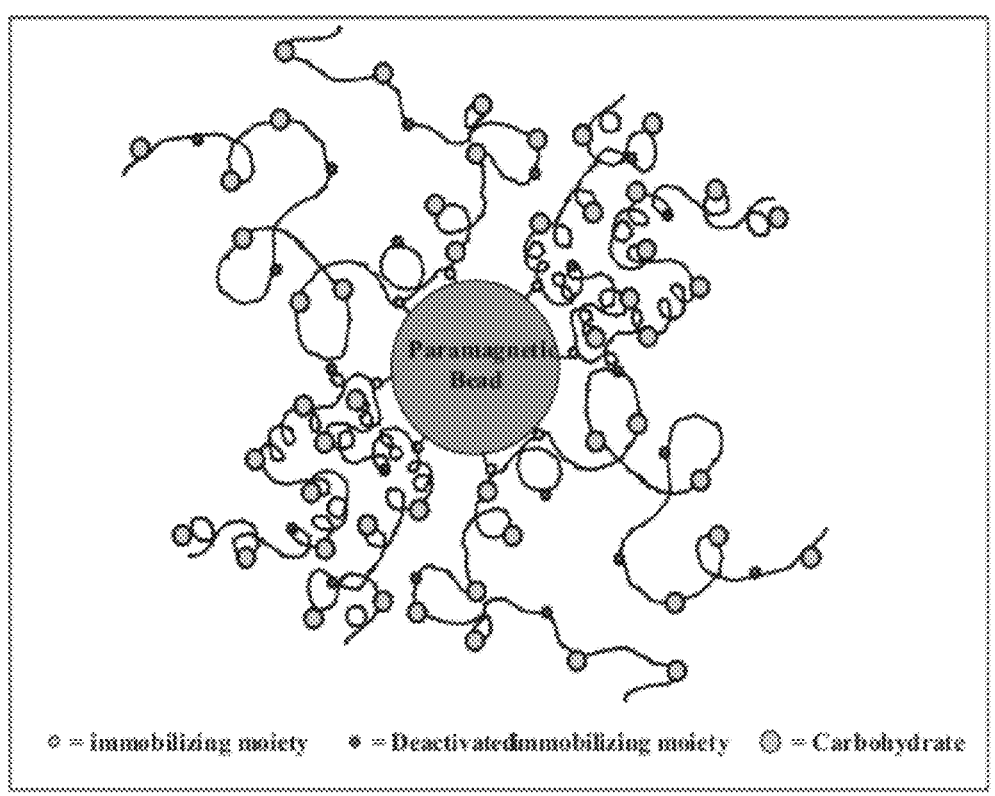
FIG. 2 schematically shows a magnetic bead with polyvalent carbohydrate pendants attached to it, according to embodiments of the present disclosure.

Among the different variety of hydrophilic polymeric chains, that may be attached to a magnetic bead, individual hydrophilic polymers can be the same or different, as desired, or some of hydrophilic polymers can be the same and some can be different, in any combination. One exemplary embodiment of the architecture of a polyvalent magnetic bead of the present disclosure is shown in FIG. 2. In this embodiment, a composition of the disclosure comprises a paramagnetic bead onto which multiple mobile scaffolds of hydrophilic polymer(s) are attached. These mobile scaffolds of hydrophilic polymer(s) are covalently immobilized on the paramagnetic bead and have carbohydrate pendants along the polymer chains.

In order to enable bonding of hydrophilic polymer(s) to a magnetic bead, the surface of a magnetic bead may be modified to include at least one functional group such as amino group. In light of the present teachings, those having ordinary skill in the art, may modify the surface of a magnetic bead in a different way and include functional groups(s) other than amino group, if desired. Non-limiting examples of such other functional groups(s) that may be present on the surface of a magnetic bead include aldehyde, alkyne, azide, biotin, N,N'-carbonyl diimidazole, carboxylate, epoxy, hydrazide, hydroxyl, iminodiacetic acid, iodoacetyl, NHS, pentadiene, silanol, streptavidin, sulfhydryl, thiol, tosyl, vinylsulfone or any combination thereof.

Figure 3:
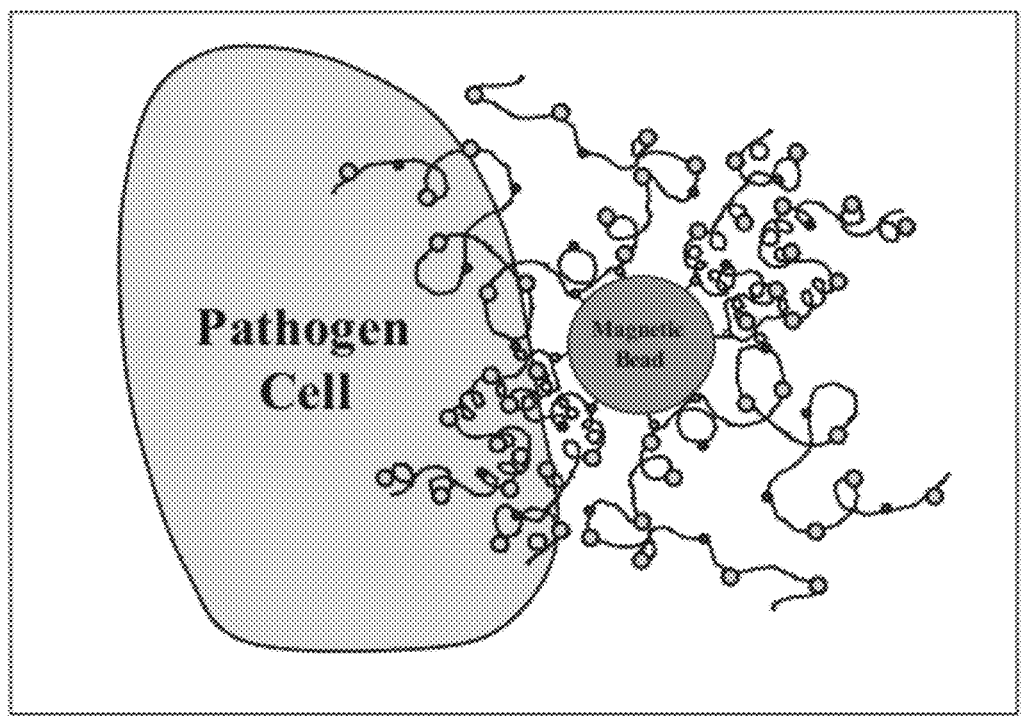
FIG. 3 schematically shows a potential mechanism of polyvalent binding of pathogen cells, according to embodiments of the present disclosure.

A mobile scaffold of hydrophilic polymer chains, such as that shown in FIG. 2, enables cell-adhesive sugar pendants to reach out into the medium (e.g., sample, diluted sample), to find binding ligands contained therein thereby greatly improving the kinetics of the binding reaction. As shown on FIG. 3, when microbes (shown as a pathogen cells) are exposed to compositions comprising polyvalent magnetic beads of the disclosure, multiple sugar pendants can latch onto the cell surfaces or envelopes of microbes resulting in multiple binding thereby enabling an applied magnetic field to extract a bound (captured) microbe from a biological sample.

The cumulative binding force due to multiple carbohydrate recognition sites is strong enough to withstand subsequent repetitive washing and rinsing to rid of debris and other undesirable materials, for example, proteins and PCR inhibitors. In addition, sugar pendants can be specially designed to selectively bind one type or strain of organism but not others. The scaffold polymer is hydrophilic by design such that it reduces, if not eliminates, non-specific adsorption of proteins and other hydrophobic biomolecules.

Various hydrophilic polymers may be used in compositions of the present disclosure. In some embodiments, use of only various functionalized copolymers or co-oligomers is contemplated, as described in more detail below, including random, alternating, graft and block copolymers, all of which are functionalized. Copolymers can be co-, ter-, quatropolymers, etc., if desired. The use of homopolymers is not contemplated.

The Hildebrand solubility parameter δ of hydrophilic copolymers that may be used can be at least about $10$ $MPa^{1/2}$, such as equal to, or greater than, about $20$ $MPa^{1/2}$, for example, equal to, or greater than about $25$ $MPa^{1/2}$. The weight-averaged molecular weight of hydrophilic copolymers that can be used can be between about 5,000 and 5,000,000 Daltons, for example, between about 50,000 and 1,000,000 Daltons, such as about 100,000 to 500,000 Daltons.

Hydrophilic copolymers comprised in compositions of the disclosure include at least two functional groups. A first functional group is to attach a hydrophilic copolymer to a magnetic bead covalently, and a second functional group (and additional functional group(s)) can be used to attach carbohydrate(s) to a hydrophilic copolymer by forming glycoconjugate(s) between the carbohydrate(s) and the hydrophilic copolymer chain(s).

In some embodiments, all the functional groups that are present in a functionalized hydrophilic copolymer are the same. In other embodiments, at least one of these functional groups is different from at least one other functional group. Those having ordinary skill in the art, in light of the present teachings, can determine which functional groups are most suitable to be included in the hydrophilic copolymer. Some non-limiting examples of functional groups that may be present in a hydrophilic copolymer to covalently link the latter to a magnetic bead include amino, hydroxyl, carboxyl, N-hydroxysuccinimide (NHS) and other reactive esters, e.g., ester of pentafluorophenol, maleimide, epoxy, aldehyde, ketone, cyanuryl, pyrrolidinedione, alkynes or azides. Covalent bonding of a hydrophilic copolymer to a magnetic bead may be via a variety of links, such as via thiol ether, an amide or a secondary amino link, or via a urea or urethane.

Some non-limiting examples of functional groups that may be present in a hydrophilic copolymer to link the latter to a carbohydrate (i.e., to form glycoconjugate(s) between the carbohydrate(s) and the hydrophilic copolymer) also include amino, hydroxyl, carboxyl, N-hydroxysuccinimide (NHS) and other reactive esters, e.g., ester of pentafluorophenol, maleimide, epoxy, aldehyde, ketone, cyanuryl, pyrrolidinedione, alkynes or azides.

One example of a class of hydrophilic polymers from which specific hydrophilic copolymer(s) can be selected is a class of acrylates bearing at least two functional groups. Non-limiting examples of suitable acrylates include functionalized copolymers having units derived from acrylic acid or methacrylic acid, copolymers of hydroxyl-substituted lower alkylacrylates and alkylmethacrylates, such as copolymers having units derived from 2-hydroxyalkyl acrylate or 2-hydroxyalkylmethacrylate, acrylamides, methacrylamides, epoxyacrylates, and derivatives of each of the above.

Another example of a class of hydrophilic copolymers from which a specific hydrophilic copolymer(s) can be selected, to form compositions of the present disclosure, is a class of poly(alkylene glycols) and alkoxy poly(alkylene glycols) bearing at least two functional groups. Non-limiting examples of such suitable poly(alkylene glycol s) include functionalized copolymers having units derived from ethylene glycol, propylene glycol and derivatives of both.

Non-limiting examples of other suitable hydrophilic copolymers that can be used in compositions of the disclosure include functionalized copolymers having units derived from alcohols, e.g., vinyl alcohol and N-vinyl lactams, such as vinyl pyrrolidone, copolymers of methylvinyl ether and maleic acid, maleic anhydride polymers and copolymers, amides, styrenesulfonates, vinylsulfonic acid, vinylsulfonates, 3-hydroxybutyric acid, urethanes, ethyleneimines, polyurethane-polyether polymers, e.g., urethane-poly(ethylene oxide) and N-vinylamides, e.g., N-vinylformamide, N-methyl-N-vinylformamide or N-methyl-N-vinylacetamide, and derivatives of each of the above.

In view of the teachings of this specification, those having ordinary skill in the art may wish to select yet (an)other hydrophilic copolymer(s), to form compositions of the present disclosure. For example, according to some embodiments, a hydrophilic copolymer used in a compositions of the present disclosure should include at least two functional groups, as explained above, and in addition a polymer is considered hydrophilic if it satisfies the hydrophilicity requirement as described herein, i.e., if a copolymer has a range of water solubility at ambient conditions from water miscible to slightly water soluble. In some embodiments, the desired degree of hydrophilicity of a copolymer, as well as other desired properties of a copolymer, may be achieved by combining with a copolymer some hydrophilic units (e.g., units formed by N,N-dimethylacrylamide) with some hydrophilic units (e.g., units formed by acrylic esters such as acrylic ester of N-hydroxysuccinimide or pentafluorophenyl acrylate), in a desired ratio. In some exemplary embodiments, an example molar ratio between more hydrophilic units and less hydrophilic units can be between about 3:1 and about 28:1, such as between about 3:1 and about 10:1.

As described in sections above, a compositions of the present disclosure generally comprises at least one glycoconjugate, i.e., a carbohydrate (i.e., sugar) moiety attached to each hydrophilic copolymer bridge. More than one kind of sugar can be attached to a (same) magnetic bead via a hydrophilic copolymer bridges. For example, the number and the kinds of carbohydrates attached to each hydrophilic copolymer bridge can be the same or can be different, in any combination.

A variety of carbohydrates may be used for the purpose of forming glycoconjugates with hydrophilic copolymer(s) in a composition of the disclosure. Non-limiting examples of carbohydrates that can be used include monosaccharides (e.g., glucose, galactose, fructose, mannose, lyxose, xylose, etc.), oligosaccharides, disaccharides (e.g., sucrose, lactose, maltose, isomaltose, lactulose, trehalose, etc.), trisaccharides, tetrasaccharides and polysaccharides (e.g., cellulose, glycan, dextrin, starches such as amylose or amylopectine, etc.), and N-modified derivatives of each.

Other examples of suitable carbohydrates include, but are not limited to, sialic acid, amine-containing saccharides and N-acylated derivatives thereof, saccharide conjugates of cyclitols and other aglycans and saccharide conjugates of aminocyclitols (e.g., aminoglycosides) and N-modified derivatives of each. In light of the present teachings, a person having ordinary skill in the art, can selected a specific carbohydrate that is most appropriate and suitable depending, inter alia, on the end use of a composition of the disclosure.

Since microbial cellular surfaces comprise a variety of complex carbohydrate structures, such as glycoproteins, glycolipids, glycosaminoglycans, and proteoglycans compositions of the disclosure can be made using the methods described herein to target specifically any particular microbe based on a particular surface moiety present on a microbe.

Several example methods for forming compositions are described in the reaction schemes described here. In one embodiment shown in Reaction Scheme I below, a hydrophilic copolymer scaffold (or bridge) can be formed by copolymer 3 prepared by copolymerization of acrylic ester of NHS 1 with N,N-dimethylacrylamide 2 as shown.

Reaction Scheme I

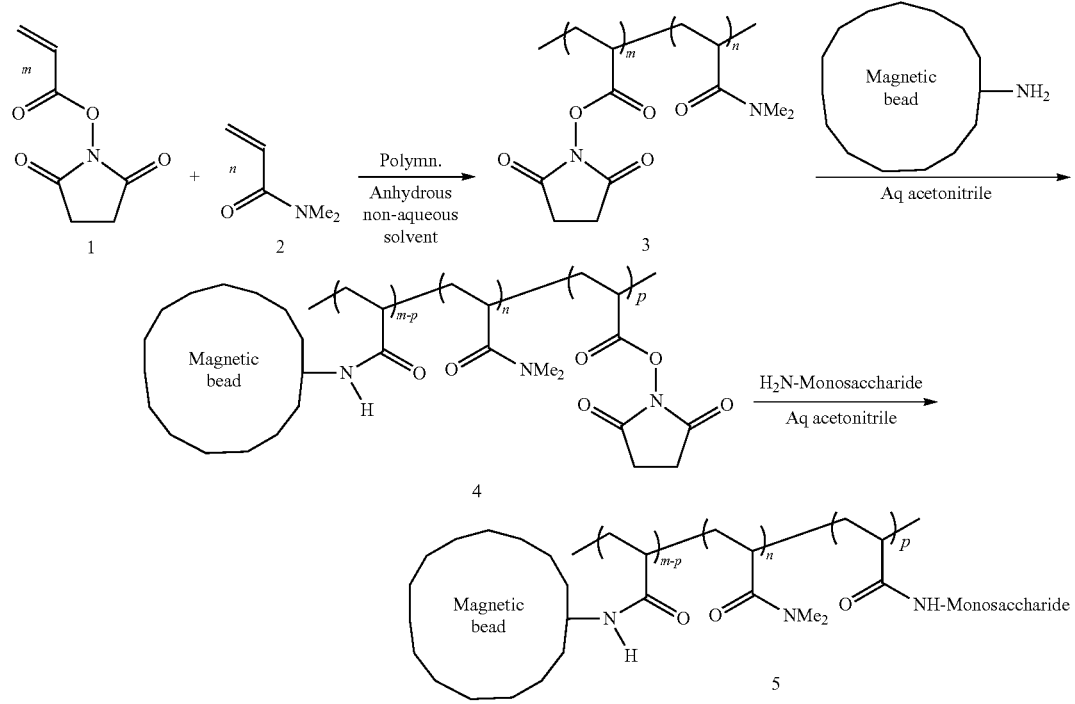

Using N,N-dimethylacrylamide (i.e., comonomer 2) imparts sufficient hydrophilicity to mobile copolymer scaffold 3, resulting in the reduction of non-specific adsorption of proteins and other hydrophobic biomolecules to a composition of the disclosure shown in this reaction, while reactive acrylate ester of NHS units enable attachment of copolymer to magnetic beads and then enable attachment of sugar(s) to the magnetic bead-bound polymer.

Copolymer 3 can be prepared to have various ratios between the N,N-dimethylacrylamide component and the acrylic ester of NHS component. Some examples of molar ratios between the N,N-dimethylacrylamide and the acrylic ester of NHS units in copolymer 3 may be between about 28:1 and 3:1, for example, between about 10:1 and 3:1. By stoichiometric control, copolymer 3 can be immobilized onto the surfaces of magnetic beads via amide link, by reacting at least a portion of the NHS ester groups with most if not all the surface amino groups on a magnetic bead to form the structure 4, which can be subsequently reacted with a sugar, such as an amino sugar, to form polyvalent magnetic bead 5.

In some embodiments, if desired, it is also possible to react a portion of NHS ester functional groups in the mobile hydrophilic copolymer scaffold 3 with an amino sugar forming a glycoconjugate prior to immobilizing itself onto an amino magnetic bead to form 5.

In order to maximize the total number of sugar pendants and minimize the number of anchoring sites along a scaffold polymer chain, an acrylic acid co-monomer can be introduced as shown in Reaction Scheme II below.

Reaction Scheme II

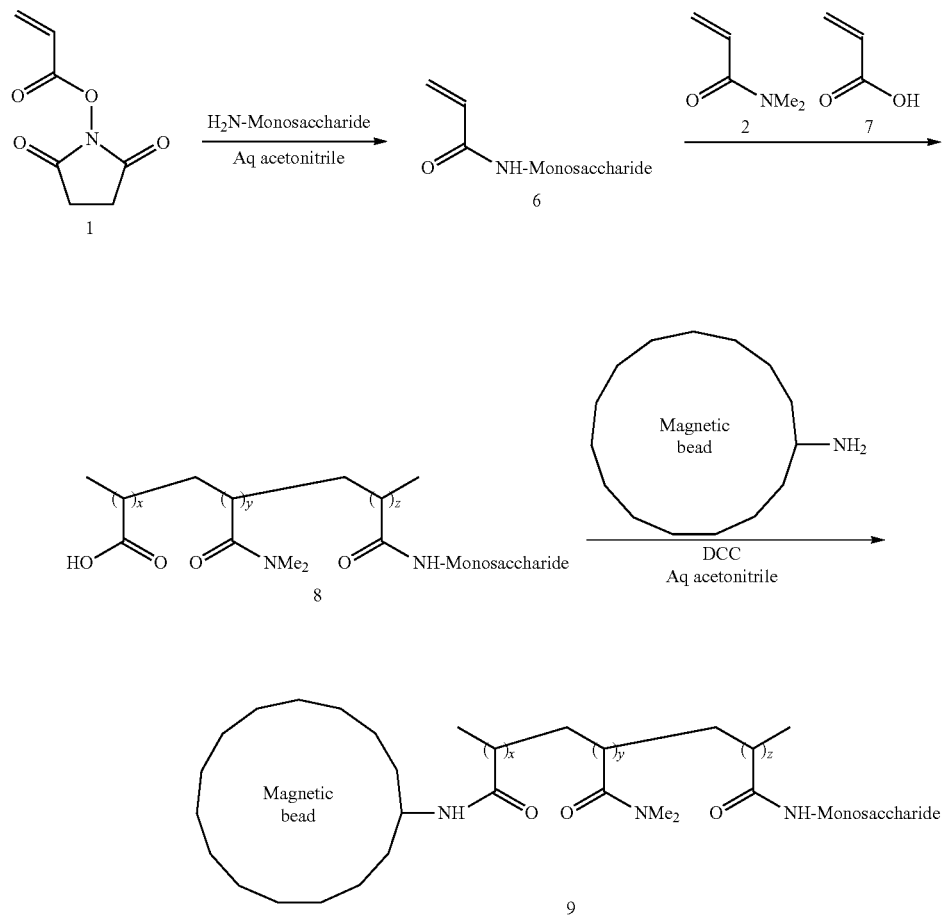

As illustrated in Reaction Scheme II, a polymerizable sugar 6 can be prepared by reacting the NHS ester of acrylic acid 1 with an amino sugar. Subsequent copolymerization of 6 with N,N-dimethylacrylamide 2 and acrylic acid 7 gives an acrylic copolymer 8 with pre-determined amount of carboxylic groups for chemical immobilization onto an amino magnetic bead to give polyvalent magnetic bead 9.

In other embodiments of the disclosure, immobilization of mobile hydrophilic copolymer scaffold onto magnetic beads can be achieved using the epoxy functionality on the polymer chain, as shown in Reaction Scheme III.

Reaction Scheme III

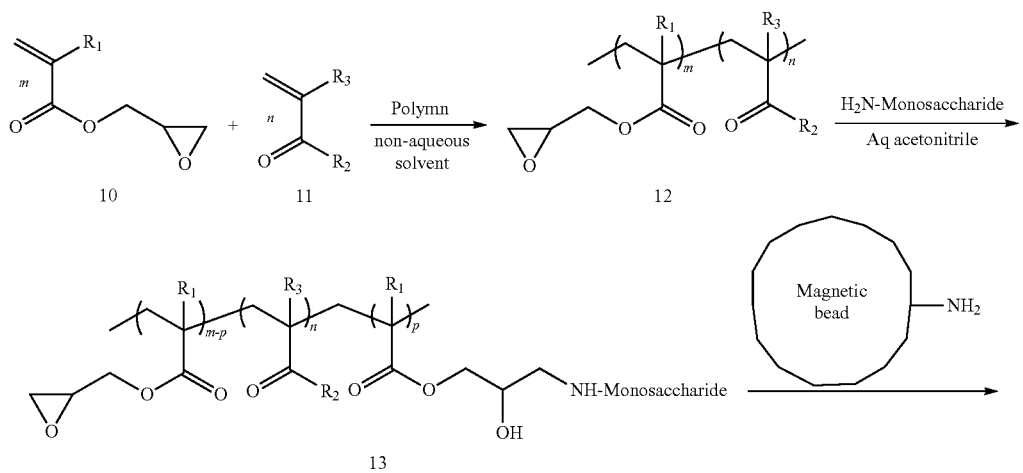

-continued

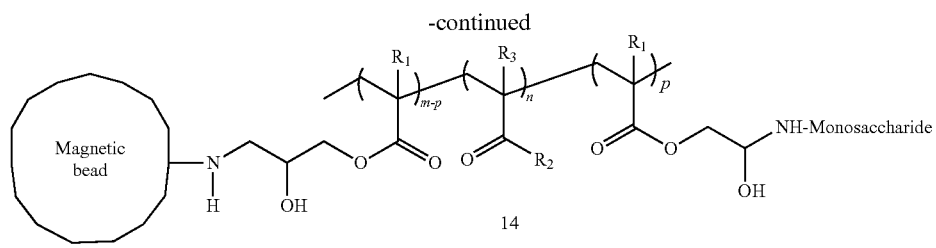

Where, $R_1$ and $R_3$ = independently H or $CH_3$, and $R_2$ = $NMe_2$ or $OCH_2CH_2OH$ As can be seen from Reaction Scheme III, the mobile hydrophilic polymer scaffold 12 can be prepared by copolymerization of glycidyl (meth)acrylate 10 and 2-hydroxyethyl (meth)acrylate 11. In some embodiments, the starting monomer 11 can be replaced by N,N-dimethylacrylamide 2 shown on Reaction Schemes I or II, above, acrylamide or a N-vinylamide. The sugar pendants can be incorporated by reacting an amino sugar with at least a portion, if not most, of the epoxy functional groups along the mobile hydrophilic polymer scaffold 12 to yield polymer 13, which subsequently immobilizes itself onto an amine-containing magnetic bead to form a secondary amino link to afford the final polyvalent magnetic bead 14.

In other embodiments, to immobilize mobile hydrophilic polymer scaffold onto magnetic beads, cyanuric chloride groups on the polymer chain may be utilized, as shown on Reaction Scheme IV.

Reaction Scheme IV

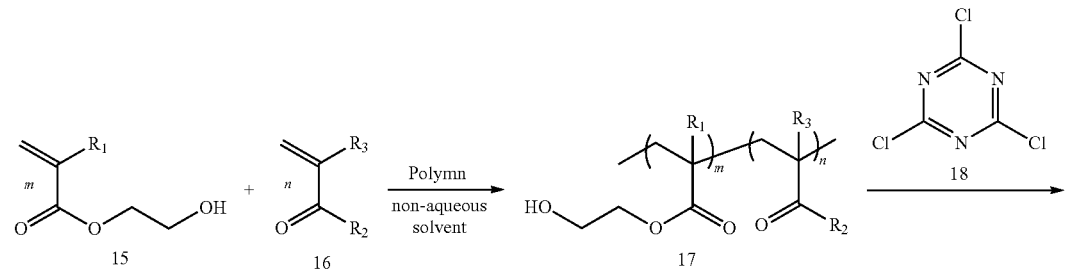

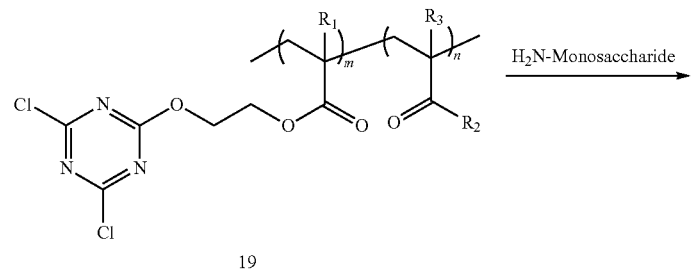

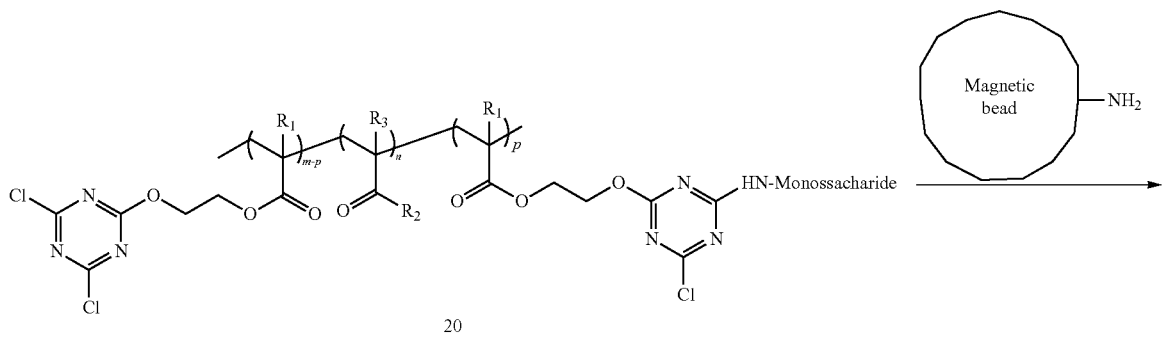

-continued

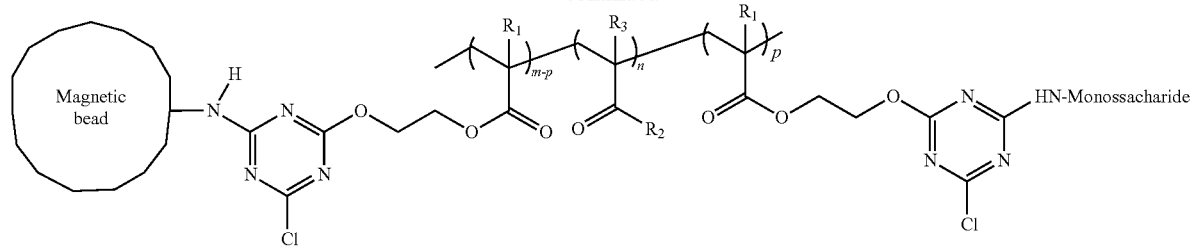

21

Where, $R_1$ and $R_3$ independently = H or $CH_3$, and $R_2$ = $NMe_2$ or $OCH_2CH_2OH$

15

As can be seen from Reaction Scheme IV, copolymer of 2-hydroxyethyl (meth)acrylate 17 can be prepared by copolymerization of 2-hydroxyethyl (meth)acrylate 15 with N,N-dimethyl (meth)acrylamide 16 that imparts high hydrophilicity to the mobile scaffold after immobilization to reduce non-specific adsorption of proteins and other hydrophobic biomolecules. Cyanuric chloride 18 can be incorporated by reacting it with copolymer 17. The feed ratio of 18 can be adjusted such that molar ratio of cyanuric chloride and 2-hydroxyethyl groups is 1:1 in copolymer 19. Sugar pendants can be introduced by reacting an amino sugar with at least a portion, if not most, of the cyanuric residues in copolymer 19 to give copolymer 20. The residual cyanuric groups in 20 can be used to immobilization onto magnetic beads to afford polyvalent magnetic beads 21.

A similar approach can be used as in another embodiment shown in Reaction Scheme V, where at least a portion of the hydroxyl pendants groups in polymer 22 can be derivatized by cyanuric chloride 18 to yield product 23 that can be subsequently reacted with an amino sugar to give polymer 24. Since the remaining two chlorides in 23 are deactivated toward hydroxyl group, further intermolecular reaction to form a crosslinked network may be negligible. Immobilizing product 24 onto an amino magnetic bead yields polyvalent magnetic bead 25. Polymer 22 can be, for example, poly(2-hydroxyethyl (meth)acrylate), poly(vinyl alcohol), poly(N-hydroxymethyl acrylamide), dextran or a polysaccharide.

Reaction Scheme V

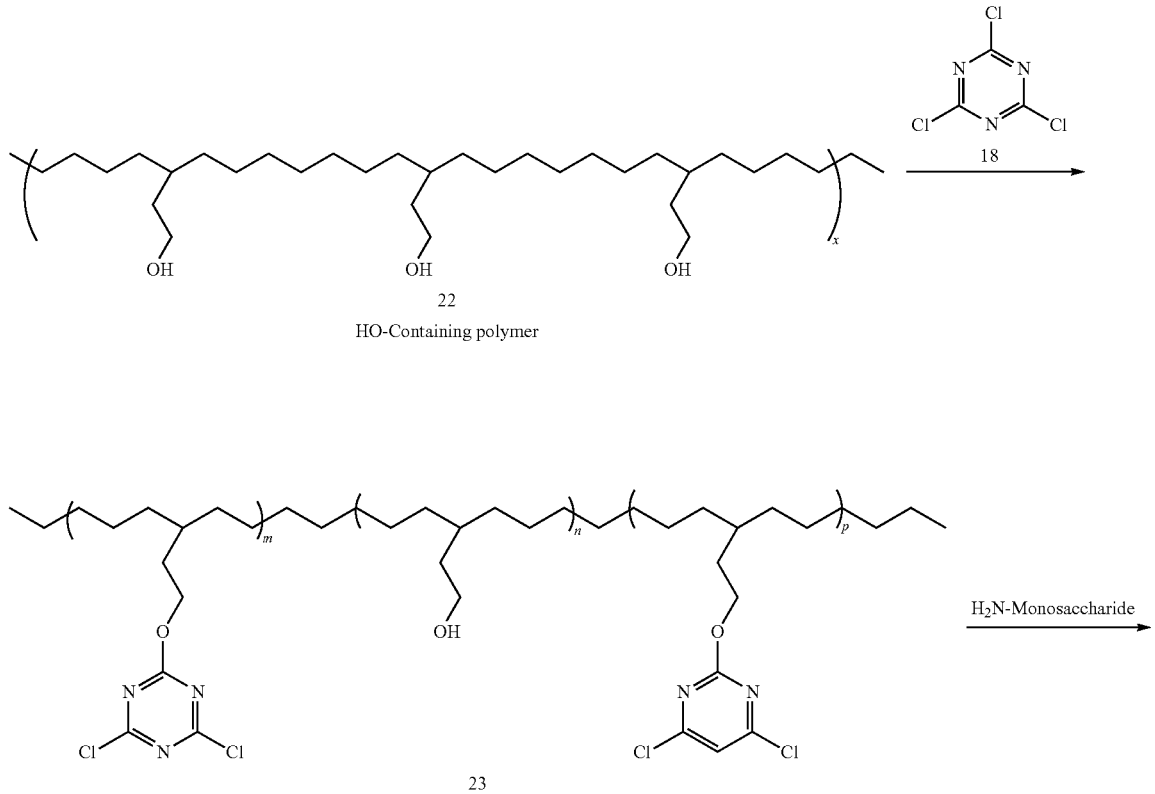

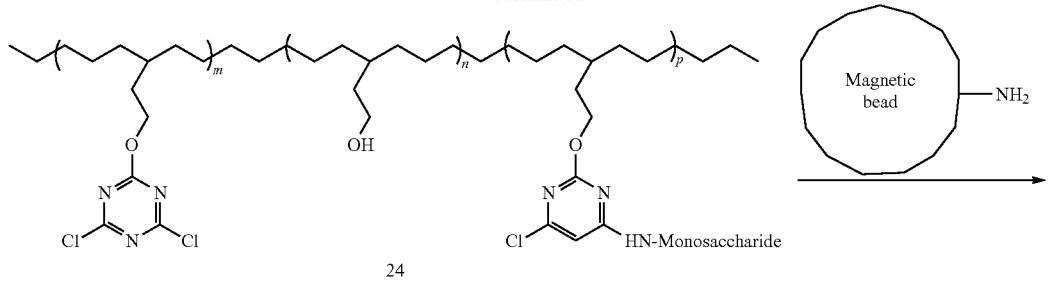

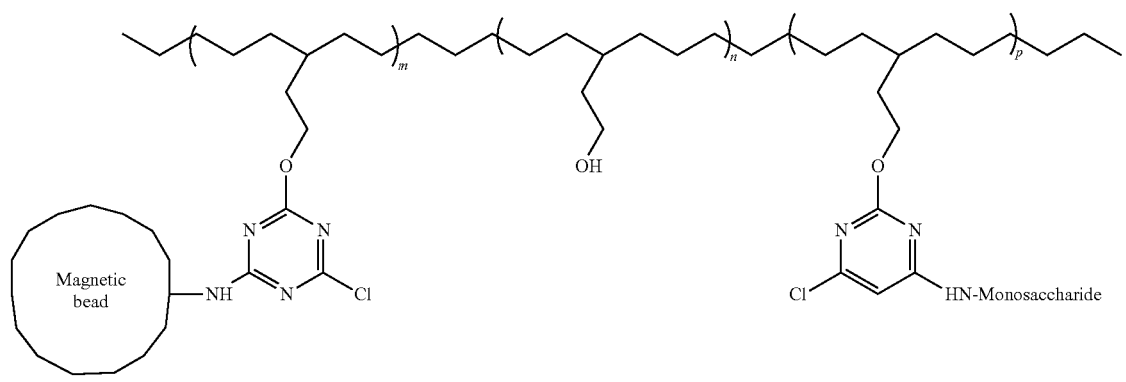

Where, x = m + n + p

In another embodiment, immobilization of mobile hydrophilic polymer scaffold onto magnetic beads can be via the formation of amide bonds (as in Reaction Schemes I and II above), while attachment of sugar residues to the polymeric matrix is via copper (I) catalyzed [3+2] cycloaddition reaction between an alkyne and an alkyl azide to form a 1,2,3-triazole, commonly known in the art as "Click" chemistry. Such a method is schematically illustrated as depicted on Reaction Scheme VI.

Reaction Schmeme VI

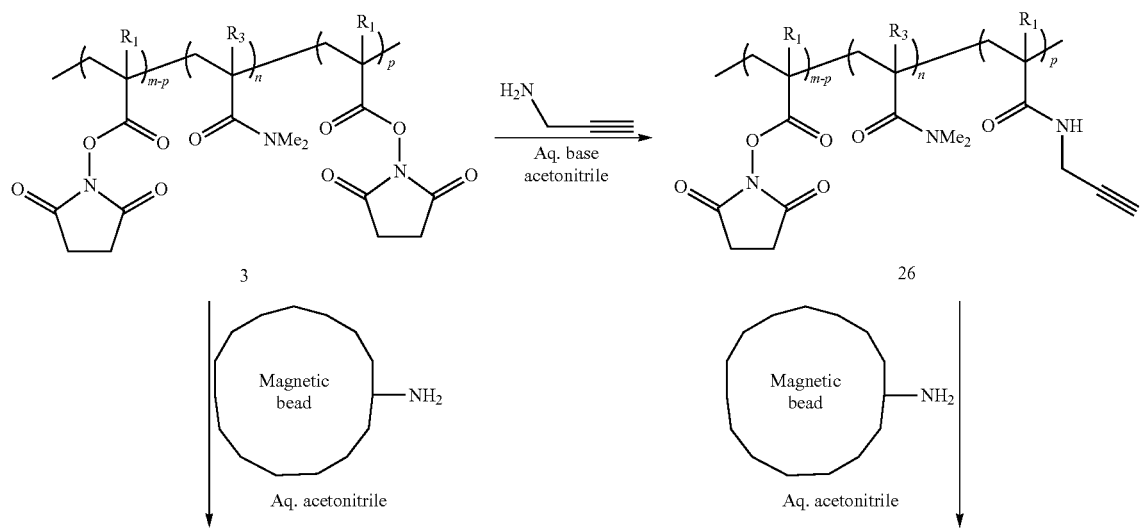

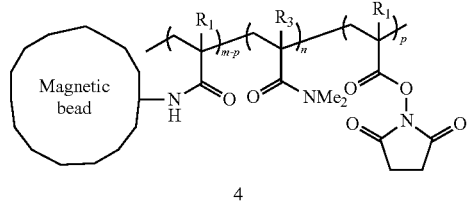 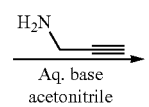 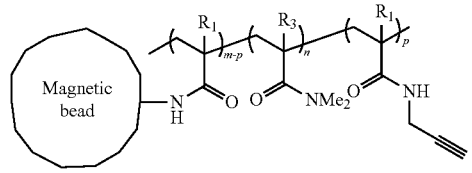

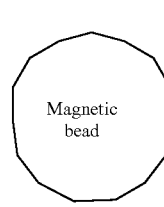

-continued

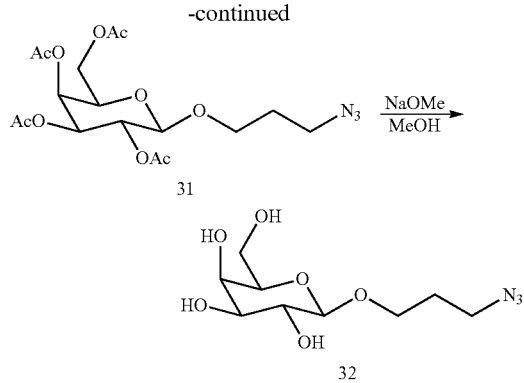

The Click approach allows putting alkyne groups in place either prior to (conversion of 3 to 26 on reaction Scheme VI), or after (4 to 27), the attachment of the polymer to magnetic beads allowing optimization of functional group stoichiometry and density on the surface of magnetic beads. Also, alkyne groups will be chemically inert during other chemical manipulations. The residual unreacted alkyne groups after sugar coupling are uncharged and stable compared to unreacted NHS-esters or epoxides.

In yet another embodiment shown in Reaction Scheme VII, glycosyl attachment of azidopropyl to saccharides can be used. Thus, for example, 1-(3-azidopropyl)-D-galactose (32) can be prepared from penta-O-acetyl-D-galactose (29) via glycosylation of trichloroacetimidate derivative (30) and then utilized in Click chemistry for the preparation of galactose linked to polymer-modified magnetic beads (product 28, Reaction Scheme VI).

Reaction Scheme VII

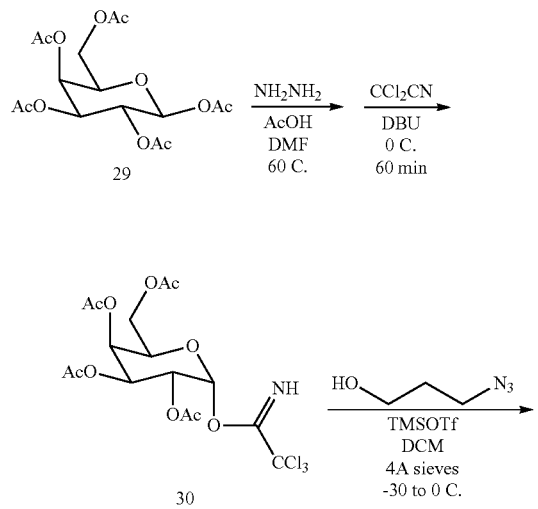

Magnetic beads having surface glycoconjugates obtained according to embodiments of the present disclosure can be used for a variety of purposes, such as, but not limited to, to methods of capturing/detecting microbial cells from samples. Methods may also comprise steps of enrichment of microbial cells captured, culturing the captured cells, lysis of captured cells to extract cellular nucleic acids and/or proteins, amplification of isolated nucleic acids from captured microbial cells (TaqMan® Probe PCR), hybridization and/or sequencing for specific identification of microbial cell types.

Various methods of using magnetic beads having surface glycoconjugates obtained according to embodiments of the present disclosure allow to isolate microbes (including viruses, pathogens, bacteria, fungi and spores thereof) from a medium (virtually any pathogen may be isolated from almost any medium). Effective rinsing/washing to remove amplification inhibitors can be also achieved. The methods of using magnetic beads having surface glycoconjugates obtained according to embodiments of the present disclosure also permit to eliminate steps such as filtration and/or centrifugation keeping isolated nucleic acids intact.

Magnetic beads having surface glycoconjugates obtained according to embodiments of the present disclosure may be used in all applications when effective and automatable capture of microorganisms from large volume (>1 mL) of complex liquid sample is required. Such applications include, but are not limited to, food pathogens detection, bioburden detection, biothreats detection and clinical applications.

The present disclosure also describes methods for capturing a population of microorganisms from a biological sample, comprising: combining a composition of the disclosure comprising: a paramagnetic bead; a plurality of hydrophilic copolymer bridges, each bridge being covalently bonded to the paramagnetic bead; and a plurality of carbohydrates, each carbohydrate being covalently bonded to the same or different hydrophilic copolymer bridge by forming a glycoconjugate with the respective hydrophilic copolymer, with the biological sample for a time to form composition-microorganism complexes; separating the composition-microorganism complexes from the sample under a magnetic field; and collecting the captured microorganisms, wherein the population of microorganisms has binding specificity for the carbohydrate.

A variety of microorganisms may be detected and/or captured using compositions of the disclosure such as bacteria including gram negative and gram positive species; viruses, fungi, and spores thereof.

In some embodiments of the method of capturing microorganisms, the population of microorganisms captured is a subpopulation of microorganisms present in the biological sample.

In some embodiments of the method, the carbohydrate is mannose and the population of microorganisms has binding specificity for mannose. For example, a microbe may have a ligand on its surface that is operable to bind mannose moieties of a composition.

A method of capturing microorganisms of the disclosure may additionally comprising downstream steps for detection and identification of the microbe. Such steps in non-limiting examples may comprise one or more of the following steps: performing a nucleic acid extraction on the captured microorganisms; Real-Time PCR analysis, culturing the captured microorganisms to increase the number of microorganisms for further analysis, DNA sequencing, immunoassays and the like.

Figure 4:
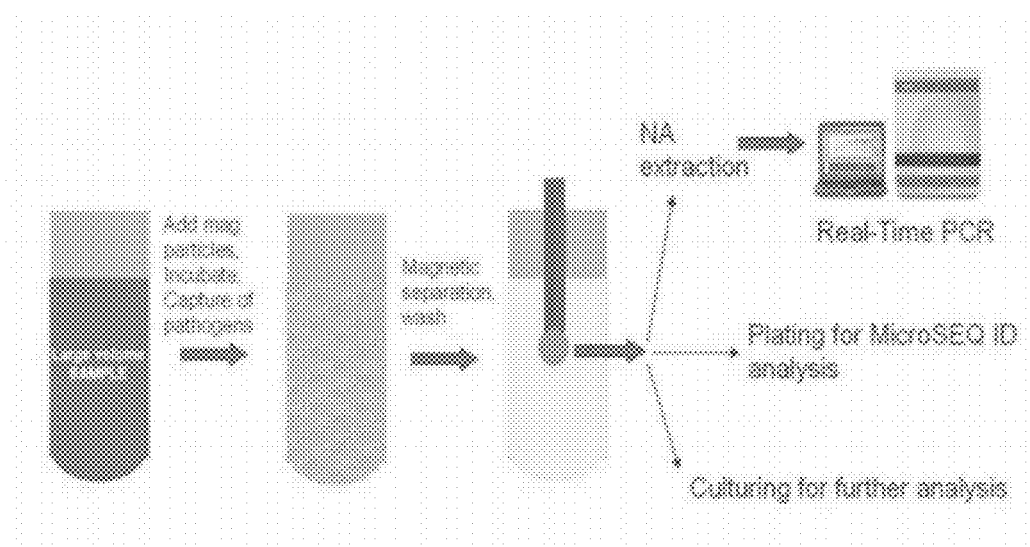
FIG. 4 schematically shows exemplary ways of using polyvalent magnetic beads, according to embodiments of the present disclosure.

In one exemplary non-limited embodiment shown schematically on FIG. 4, one process of using polyvalent magnetic beads of the present disclosure to capture, enrich, and identify pathogenic microorganism may be illustrated as follows:

(1) the polyvalent magnet beads may be added into a biological sample and incubated, followed by (2) separating the magnetic beads under a magnetic field;

(3) washing the magnetic beads to rid of debris and non-pathogenic materials; and (4) dividing the captured pathogenic microorganism for DNA extraction/Real-Time PCR, plating for MicroSEQ ID analysis, and culturing for further analysis.

In contrast to the "monovalent" binding of a pathogen cell onto a carbohydrate-modified magnetic bead as shown in FIG. 1 and described in published U.S. Patent Application No. 2009/0186346A1, which has weak affinity, efficiency and binding strength, compositions of the present disclosure provide "polyvalent" binding that is able to withstand repetitive washing and rinsing to remove debris and undesirable materials from a biological sample from which capture/separation/detection of a microbe is desired.

EXAMPLES

The disclosure will be further described by the following examples, which are intended to be purely exemplary of the disclosure and not to limit its scope in any way. Where cited NMR chemical shifts are in ppm ($\delta$) and relative to the position of the solvent peak.

Example 1

Preparation of Copolymer of N,N-Dimethylacrylamide and Acrylic Acid Ester of N-hydroxysuccinimde (First Ratio Between Monomers)

Polymerization was carried out in a 250-mL round bottom glass flask with three 14/20 ground glass joints, equipped with a half-inch magnetic stir bar, a water-cooled condenser connected to the first joint, and a rubber septum with a glass bleeding tube for dry argon purging in the second joint. The water-cooled condenser was equipped with a rubber septum with a 10-gauge stainless steel syringe needle for venting into a mineral oil bubbler. A ground glass stopper was placed in the third joint. All reagents were obtained from Sigma-Aldrich and were used as received except for N,N-dimethylacrylamide that had been vacuum distilled prior to use.

The reaction flask was charged with 100 mL of anhydrous acetonitrile, 4.0371 g (40.725 mmole) of N,N-dimethylacrylamide, 0.2473 g (1.462 mmole) of acrylic acid ester of N-hydroxysuccinimde and 0.0306 g (0.123 mmole) of azobis(2,4-dimethylvaleronitrile). The molar ratio of the N,N-dimethylacrylamide and acrylic acid ester was 28:1. Under constant 150 rpm stirring at ambient temperature, the mixture was purged by bubbling ultra pure argon for 60 minutes at a flow rate of 60 mL/min. The reaction flask was then immersed in an oil bath at 55° C. and stirred at 150 rpm for 16 hours under argon atmosphere. The reaction solution was cooled to ambient temperature under argon atmosphere prior to be used for conjugating carbohydrate molecules onto magnetic beads having surface amino groups.

Example 2

Preparation of Copolymer of N,N-Dimethylacrylamide and Acrylic Acid Ester of N-hydroxysuccinimde (Second Ratio Between Monomers)

The experimental setup and polymerization conditions were the same as described in Example 1. The reaction flask was charged with 100 mL of anhydrous acetonitrile, 3.5192 g (35.501 mmole) of N,N-dimethylacrylamide, 1.9566 g (11.571 mmole) of acrylic acid ester of N-hydroxysuccinimde, and 0.0343 g (0.128 mmole) of azobis(2,4-dimethylvaleronitrile). The molar ratio of the N,N-dimethylacrylamide and acrylic acid ester was 3:1.

Example 3

Preparation of Copolymer of N,N-Dimethylacrylamide and Pentafluorophenyl Acrylate (First Ratio Between Monomers)

The experimental setup and polymerization conditions were the same as described in Example 1. All reagents were obtained from Sigma-Aldrich except for pentafluorophenyl acrylate (95% pure) which was obtained from Polysciences. N,N-dimethylacrylamide was vacuum distilled prior to use. The reaction flask was charged with 50 mL of anhydrous acetonitrile, 3.0728 g (30.997 mmole) of N,N-dimethylacrylamide, 1.7538 g (7.366 mmole) of pentafluorophenyl acrylate, and 0.0315 g (0.127 mmole) of azobis(2,4-dimethylvaleronitrile). The molar ratio of the N,N-dimethylacrylamide and pentafluorophenyl acrylate was 4.2:1.

Example 4

Preparation of Copolymer of N,N-Dimethylacrylamide and Pentafluorophenyl Acrylate (Second Ratio Between Monomers)

The experimental setup and polymerization conditions were the same as described in Example 3. The reaction flask was charged with 50 mL of anhydrous acetonitrile, 3.1147 g (31.421 mmole) of N,N-dimethylacrylamide, 2.5027 g (10.511 mmole) of pentafluorophenyl acrylate, and 0.0348 g (0.140 mmole) of azobis(2,4-dimethylvaleronitrile). The molar ratio of the N,N-dimethylacrylamide and pentafluorophenyl acrylate was 3:1. The relative incorporation of the two acrylate monomers was determined by NMR by the method of Eberhardt et al, *Eur. Polymer J.*, 41, 1569-75 (2005)).

A crude reaction solution of the copolymer in acetonitrile, nominally containing 500 mg of dissolved polymer, was evaporated and dried under vacuum. The residue was taken up in dry benzene (5 mL), and then added dropwise to a flask of rapidly stirring hexane (50 mL). After several minutes the flask was placed in the freezer overnight, whereafter a fine solid material settled out. The supernatant was decanted and the residue was rinsed in-situ with hexane, and then re-precipitated from benzene/hexane as before. After vacuum drying, 409 mg of the polymer was obtained as an amorphous white solid with faint odor of acrylates.

By $^1$H-NMR (400 MHz, ACN-d3) the polymer is essentially free of unpolymerized acrylates. $^{13}$C-NMR indicates three carbonyl signals ($\delta$ 171.1, 174.5, 175.2 ppm) in an approximately 4:1:1 ratio, corresponding respectively to dimethylamide, pentafluorophenyl ester, and free carboxylic acid functionality). $^{19}$F-NMR shows three broadened signals ($\delta$ −164.2, −159.8, −154.1 ppm) for the pentafluorophenyl ester in a 2:1:2 ratio.

Example 5

Preparation of Copolymer of N,N-Dimethylacrylamide and Pentafluorophenyl Acrylate (Third Ratio Between Monomers)

The experimental setup and polymerization conditions were the same as described in Example 3. The reaction flask was charged with 50 mL of anhydrous acetonitrile, 1.0423 g (10.514 mmole) of N,N-dimethylacrylamide, 2.3924 g (10.048 mmole) of pentafluorophenyl acrylate, and 0.0169 g (0.068 mmole) of azobis(2,4-dimethylvaleronitrile). The molar ratio of the N,N-dimethylacrylamide and pentafluorophenyl acrylate was 1.1:1.

Example 6

Synthesis of 1-(4-Aminobutyl)-β-D-Mannose (Scheme VIII)

The synthesis of the title compound 37 was conducted as shown on the Reaction Scheme VIII Reaction Scheme VIII

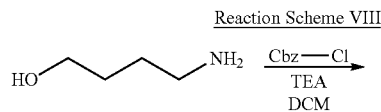

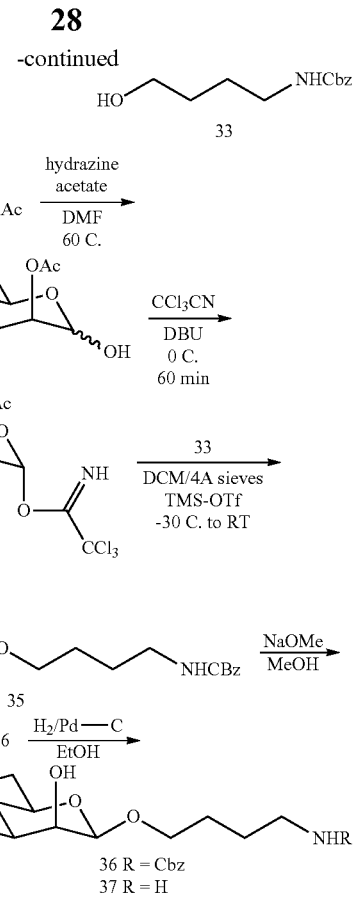

4-(N-Benzyloxycarbonylamino)butan-1-ol (33, Reaction Scheme VIII) was prepared by the method of Boseggia et al. (*J. Am. Chem. Soc.*, 126, 4543-9 (2004)). 2,3,4,6-tetra-O-acetyl-D-mannosyl trichloroacetimidate (34) was prepared by adapting the method of Cheng et al. (*J. Med. Chem.*, 48, 645-52 (2005)), whereby, commercially available (Sigma) D-mannose pentaacetate (12.6 g, 32.4 mmol) in DMF (60 mL) was warmed to 60° C. under Ar. To this was added a suspension of hydrazine acetate salt (3.58 g, 38.9 mmol) in DMF (15 mL) and the mixture was stirred overnight at ambient temperature. The reaction was diluted into ethyl acetate (EtOAc), washed with water several times, then dried to afford 2,3,4,6-tetra-O-acetyl-D-mannose (6.85 g, 61%).

2,3,4,6-tetra-O-acetyl-D-mannose so obtained was dissolved in dry dichloromethane (DCM) (100 mL) and chilled in an ice bath, and to this was added trichloroacetonitrile (27.4 g, 190 mmol), followed by dropwise addition of an ice-cold solution of 1,8-diazabicyclo[5.4.0]undec-7-ene (DBU) (6.08 g, 40 mmol) in DCM (50 mL). The reaction was stirred to room temperature, then concentrated under vacuum to give a viscous yellow oil which was purified by silica column chromatography (hexane-EtOAc, 100:0 to 1:2) to give 4.48 g pure trichloroacetimidate (34) (28% overall yield from D-mannose pentaacetate).

$^1$H-NMR (CDCl$_3$): $\delta$ 8.78 (s, 1H), 6.27 (d, J=1.8 Hz), 5.46 (s, 1H), 5.39 (m, 3H), 4.19 (m, 3H), 2.19 (s, 3H), 2.08 (s, 3H), 2.06 (s, 3H), 2.00 (s, 3H). $^{13}$C-NMR (CDCl$_3$): $\delta$ 170.66, 169.89, 169.81, 169.70, 159.73, 94.52, 71.22, 68.84, 67.88, 65.38, 62.06, 21.02, 20.85, 20.77, 20.69.

Next, protected mannosyl aminoglycoside (35) was prepared by reaction of a solution of carbobenzyloxy(Cbz)-aminoalcohol (33) (0.54 g, 2.4 mmol) and trichloroacetimidate (34) (0.79 g, 1.6 mmol) in dry DCM (12 mL) containing 100 mg of 4 Å molecular sieves, in a dry-ice bath (temperature below −30 C), with dropwise addition of trimethylsilyl trifluoromethanesulfonate (also known as TMS-triflate) (290 µL, 1.6 mmol) under Ar. The reaction was stirred to ambient temperature overnight, then diluted with DCM and washed successively with aq. bicarbonate, water, and saturated NaCl. After evaporation and drying, a white residue was obtained which was purified by silica column (hexane-EtOAc, 90:10 to 2:1) to give 372 mg (0.67 mmol, 42%) of product compound (35) as an amorphous white solid. MS (ESI): [M+H]+=554.4.

Next, tetraacetate (35) (0.89 g, 1.6 mmol) was dissolved in methanol (40 mL) and treated with 25% sodium methoxide in methanol (1.45 mL, 4 equivalents) for 3 hrs, then the mixture was partially concentrated, poured into cold water, and acetic acid was added to pH 5. The solution was lyophilized to give 1-(4-N-Cbz-aminobutyl)-β-D-mannose (36) (0.61 g, 100%). MS (ESI): [M+Na]+=408.2. This material was dissolved in ethanol (40 mL) containing acetic acid (50 µL), charged with 5% Pd—C catalyst (100 mg) and hydrogenated overnight under 1 atm pressure to quantitatively remove the Cbz protecting group, to give 1-(4-aminobutyl)-β-D-mannose (37) as the acetate salt (0.49 g, 100%). $^{13}$C-NMR (MeOH-d4): δ 101.65, 74.71, 72.47, 72.09, 68.41, 67.92, 62.43, 44.96, 27.71, 27.61. The material was sufficiently pure for subsequent use.

Example 7

Preparation of Mannose-M270 Beads

A well-dispersed suspension of 100 µL Dynabeads M-270 Amine magnetic microspheres (nominally 60M beads, in supplied buffer) was pipetted into a 1.5 mL centrifuge tube. Beads were separated magnetically, the buffer was aspirated, then beads were washed with 100 mM HEPES pH 7.0 (2×150 µL), and beads were aspirated and left moist in the tube. Reactive polymer DMA-PFP 3:1, 180 mg, was dissolved in acetonitrile (500 µL), then 100 mM HEPES pH 8.0 was added (33 µL), and then the polymer solution was added to the tube containing the beads. The mixture was agitated by rapid vortexing until beads were well-dispersed, then the tube was placed in a heated vortexing mixer (35° C., 1400 rpm) for 3 hrs, with occasional removal of the tube and vigorous vortexing to keep beads well-dispersed. The bead suspension was magnetically separated, beads were washed with 100 mM HEPES pH 7 (3×300 µL), then polymer-coated beads were drained.

In another tube was placed a solution of 1-β-(4-aminobutyl)-D-mannose prepared as described in Example 6 (75 mg, 0.30 mmol) in 100 mM HEPES pH 8.0 (pH checked by meter). The amino-saccharide solution was then introduced and the beads were re-suspended, dispersed, and reacted at 35° C./1400 rpm. After 2 hrs, the beads were separated, washed with HEPES pH 7 (3×300 µL), then resuspended in buffer (500 µL) and treated with a solution of 40% aq. dimethylamine (50 µL) to cap any remaining reactive esters. After vortexing for several minutes, the beads were drained and washed with 100 mM HEPES pH 7 (3×300 µL). After draining the beads were re-suspended and stored in 300 uL of the same buffer.

Example 8

Recovery of FimH+ Containing Bacteria by Polyvalent Mannose Bead

To demonstrate that polyvalent glycoconjugate magnetic beads made according to embodiments of the present disclosure can be used to recover specific microbes from solution, mannose was coupled to a copolymer of N,N-dimethylacrylamide and acrylic ester of NHS conjugated to a magnetic bead. The molar ratio between the N,N'-dimethylacrylamide units and the acrylic ester of NHS units was between 3:1 and 4:1. This bead was used to recover bacteria previously shown to bind to mannose containing substrates. The mannose binding E. coli K-12 strain KB54 and E. coli AAEC356 were used (J. Biol. Chem., 272, 17880-17886 (1997) and J. Bact. 175, 4335-4344 (1993)). The KB54 strain expresses large numbers of mannose binding type 1 fimbriae from a plasmid and is known to have a high affinity for mono-mannose coupled BSA. The E. coli strain AAEC356 constitutively expresses type 1 fimbriae and is known to bind to surfaces coupled with mannose containing RNase B even after rigorous washes.

The bacterial stain KB54 was obtained from E. V. Sokurenko at the University of Washington, and the strain AAEC356 from I. C. Blomfield at the University of Kent. KB54 cells were grown over night at 37° C. without shaking in Brain Heart Infusion broth containing 100 µg/ml ampicillin and 25 µg/ml chloramphenicol (Sigma). AAEC356, E. coli 0157:H7, Listeria monocytogenes, and Salmonella typhimurium were also grown overnight at 37° C. without shaking in Brain Heart Infusion broth, but without supplemental antibiotics.

Prior to recovery of bacteria with polyvalent glycoconjugate beads, cells were diluted 1×10$^6$ fold with binding buffer (phosphate buffered saline (Invitrogen) containing 1 mM calcium chloride, 1 mM magnesium chloride, and 0.05% Tween20 (Sigma)) to approximately 1,000 cells/ml. To recover the bacteria, 1 ml of diluted cells was added to 0.3 mg of the beads in a 1.5 ml Eppendorf microcentrifuge tube. Beads were incubated with the cells at room temperature with gentle mixing by rotation for 30 min. After 30 min, the tubes were placed in a Dynal MPC-S rack containing its magnet (Invitrogen). After magnetic separation (~3 min) the supernate was removed, and 100 µl of Rapid Spin Lysis Solution was added (Applied Biosystems).

To determine the value of 100% recovery of cells, 5 µl of a 5,000 fold dilution of the overnight culture was added to 95 µl Rapid Spin Lysis Solution and 0.3 mg beads. Listeria containing samples were adjusted to 2 U/ul Protease K and heated at 56° C. for 30 min. All the tubes were heated for 10 min at 95° C. and spun for 3 min at maximum rpm in an Eppendorf microcentrifuge. For E. coli strains, supernate (2 µl) was added to EMMv2 Master Mix (18 µl) containing E. coli Taqman primers. The mixture was thermocycled on the ABI 7500 following the 7500 standard protocol. Before addition of heated E. coli 0157:H7, Listeria or Salmonella samples to lyophilized RT-PCR reagents, heat treated samples were diluted 1:5 with water. The amount of 30 µl of sample was added to the MicroSeq lyophilized RT-PCR reagents (Applied Biosystems).

It was determined that the polyvalent mannose bead recovers E. coli type 1 fimbriae expressing strain cells, but not E. coli 0157:H7, Listeria or Salmonella. Briefly, as described above, cells were incubated with control magnetic beads (beads coupled with polymer only) and separately with polyvalent mannose beads (beads coupled with polymer and then coupled with mannose). The beads were magnetically drawn to the bottom of a tube and the supernate containing unbound cells was removed. The cells captured by the beads were quantified by Real-Time PCR. The results with AAEC356 cells are shown on FIG. 5, and demonstrate that bacteria can be efficiently recovered by polyvalent mannose magnetic beads.

Figure 5:
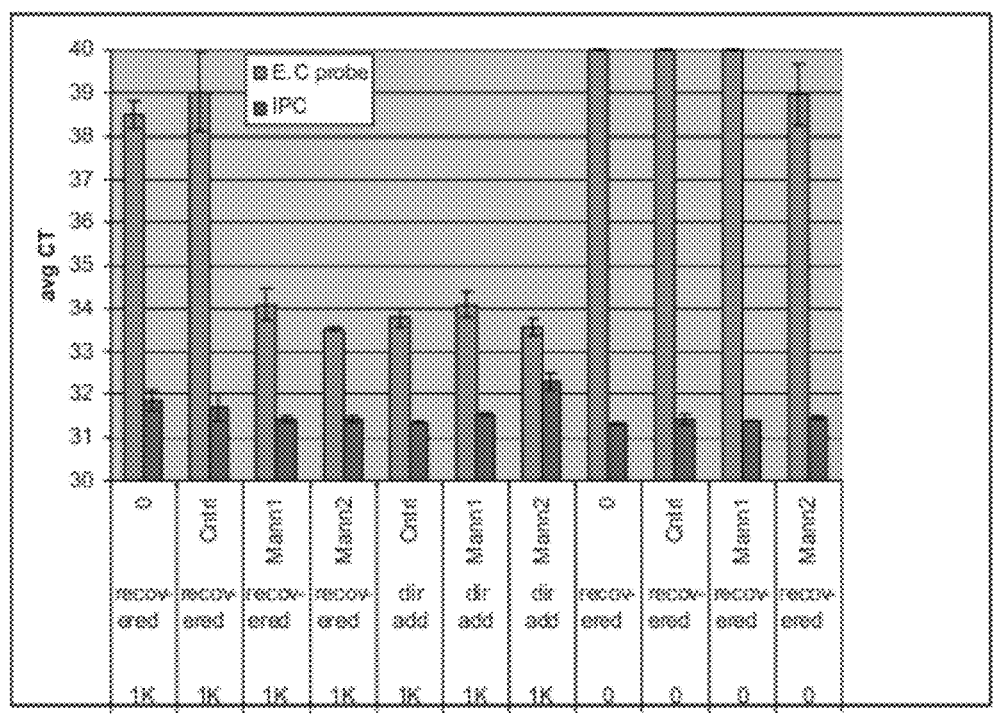
FIG. 5 shows results of a real-time PCR analysis of E. coli strain AAEC356 recovery by polyvalent mannose magnetic beads prepared according to one embodiment of the present disclosure.

In FIG. 5, the results with the Taqman probe against *E. coli* (E.C. probe) are shown by the bars on the left hand side in each pair and results with the internal control probe (IPC) against a plasmid added to all samples are shown by the bars on the right hand side. The "avg CT" or average cycle threshold is the thermocycle were the fluorescence is significantly above background. The "avg CT" represents four values—two PCR reaction duplicates of two sample replicates. "Recovered" represents RT-PCR reactions with cells recovered by the beads, whereas "Dir add" refers to a known number of cells equal to 100% recovery by the beads added directly to the RT-PCR reaction. Cell number (Cell#) equal to zero controls were included to detect any contamination of the beads with *E. coli*. prior to the addition of AAEC356 cells."Cntrl" represents control beads coupled with copolymer only (i.e., the above-mentioned copolymer of N,N'-dimethylacrylamide and acrylic ester of NHS having the molar ratio between the N,N'-dimethylacrylamide units and the acrylic ester of NHS units between 3:1 and 4:1), and "Mann1" and "Mann2" represent beads where the mannose was reacted with the polymer for 30 and 180 min respectively.

The 80-100% recovery of AAEC356 cells by the polyvalent mannose beads was determined by comparing the Ct of samples containing recovered cells with the Ct obtained from cells added directly to the RT-PCR reaction (Table 1). The control bead did not recover any cells. The three pathogens did not show an affinity for mannose since the recoveries with the control and mannose-beads were similar (Table 1). Data was collected and analyzed as described for AAEC356 on FIG. 5.

TABLE 1

| Bacteria | % Average Recovery | | |
|---|---|---|---|
| | Control Bead | Mannose Bead 1 | Mannose Bead 2 |
| *E. coli* AAEC356 | <1 | 90 ± 10 | 100 |
| *E. coli* KB54 | <4 | 40 ± 20 | 40 ± 20 |
| *E. coli* 0157: H7 | <1 | <1 | <1 |
| *Listeria* | 12 ± 6 | 12 ± 6 | <1 |
| *Salmonella* | 4 | 2 ± 1 | 3 |

The failure to recover the pathogens tested with the polyvalent mannose beads could be due to the particular strains of pathogens used not expressing any or sufficient mannose binding fimbriae to capture the level of mannose currently coupled to the bead. Some *E. coli* 0157:H7 and *Salmonella typhimurium* strains do not express type 1 fimbriae, and these fimbriae are not noted in *Listeria*.

Although only a few embodiments have been described in detail and exemplified above, those having ordinary skill in the art will clearly understand that many modifications are possible in the described embodiments without departing from the teachings thereof. All such modifications are intended to be encompassed within the following claims.

What is claimed is:

1. A composition, comprising:
   (a) a paramagnetic bead;
   (b) a plurality of hydrophilic copolymer bridges, each bridge being covalently bonded to the paramagnetic bead; and
   (c) a plurality of carbohydrates, each carbohydrate being covalently bonded to the same or different hydrophilic copolymer bridge by forming a glycoconjugate with the respective hydrophilic copolymer, wherein each hydrophilic polymer bridge is bonded to the paramagnetic bead via a link formed by an amino group, wherein at least one hydrophilic copolymer is different from at least one other hydrophilic copolymer.

2. The composition of claim 1, having the structure:

$$MB-(HP)_n-(S)_m,$$

wherein MB is a magnetic bead; HP is hydrophilic polymer bridge; S is a carbohydrate; and each of n and m is an integer, wherein n≥1 and m≥1, with the further proviso that if n=1, then m≥2.

3. The composition of claim 1, wherein the paramagnetic bead is DYNABEADS®.

4. The composition of claim 1, wherein the hydrophilic copolymer bridges are formed of functionalized hydrophilic copolymers selected from the group consisting of functionalized acrylates, poly(alkylene glycols), alkoxy poly(alkylene glycols), copolymers of methylvinyl ether and maleic acid, urethanes, ethyleneimines, polyurethane-polyether copolymers, copolymers having units derived from vinyl alcohol, N-vinyl lactams, vinyl pyrrolidone, amides, maleic anhydride, styrenesulfonates, vinylsulfonic acid, vinylsulfonates, N-vinylamides or 3-hydroxybutyric acid.

5. The composition of claim 4, wherein the functionalized acrylates are selected from the group consisting of functionalized copolymers having units derived from acrylic acid, methacrylic acid, 2-hydroxyalkyl acrylate, 2-hydroxyalkyl-methacrylate, acrylamides, methacrylamides, epoxy-acrylates.

6. The composition of claim 4, wherein each of the functionalized hydrophilic copolymers includes a plurality of functional groups, comprising:
   (a) a first functional group to form a covalent linkage between the magnetic bead and the respective hydrophilic copolymer bridge; and
   (b) at least one second functional group, to attach at least one carbohydrate to the hydrophilic copolymer by forming glycoconjugate(s) between the carbohydrate(s) and the hydrophilic copolymer.

7. The composition of claim 6, wherein in the plurality of functional groups the functional groups are the same.

8. The composition of claim 6, wherein in the plurality of functional groups at least one functional group is different from at least one other functional group.

9. The composition of claim 6, wherein the functional groups are independently selected from the group consisting of an amino, hydroxyl, carboxyl, N-hydroxysuccinimide, an ester of pentafluorophenol, maleimide, an epoxy, an aldehyde, a ketone, a cyanuryl, a pyrrolidinedione, an alkyne and an azide.

10. The composition of claim 1, wherein the carbohydrates comprise monosaccharides, disaccharides, trisaccharides, tetrasaccharides, oligosaccharides or polysaccharides.

11. The composition of claim 10, wherein the monosaccharides are independently selected from the group consisting of glucose, galactose, fructose, mannose, lyxose and xylose.

12. The composition of claim 10, wherein the disaccharides are independently selected from the group consisting of sucrose, lactose, maltose, isomaltose, lactulose and trehalose.

13. The composition of claim 10, wherein the polysaccharides are independently selected from the group consisting of cellulose, glycan, dextrin, amylase and amylopectine.

14. The composition of claim 1, wherein the carbohydrates are independently selected from the group consisting of sialic acid, amine-containing saccharides, saccharide conjugates of glycans and saccharide conjugates of aminocyclitols.

15. The composition of claim 1, wherein each carbohydrate is the same.

16. The composition of claim 1, wherein at least one carbohydrate is different from at least one other carbohydrate.

17. The composition of claim 1, wherein each hydrophilic copolymer has the Hildebrand solubility parameter δ of at least about 10 MPa$^{1/2}$.

18. The composition of claim 1, wherein each hydrophilic copolymer has the weight-averaged molecular weight of between about 5,000 and about 5,000,000 Daltons.

19. A method for fabricating a paramagnetic bead composition, the method comprising:
(a) immobilizing a plurality of functionalized hydrophilic copolymers on the surface of a paramagnetic bead; and
(b) bonding at least one carbohydrate to each of at least two hydrophilic copolymers, wherein each of the functionalized hydrophilic copolymers includes a plurality of functional groups, comprising a first functional group and at least one second functional group, to thereby obtain the paramagnetic bead composition, wherein the step of bonding comprises reacting the plurality of functionalized hydrophilic copolymers with the carbohydrate(s), wherein at least two glycoconjugates are formed between at least one carbohydrate and the hydrophilic copolymers, wherein the step of immobilizing comprises reacting the plurality of functionalized hydrophilic copolymers with the paramagnetic bead, wherein a covalent linkage is formed between the paramagnetic bead and each hydrophilic copolymer.

20. The method of claim 19, wherein the hydrophilic copolymers are functionalized and selected from the group consisting of functionalized acrylates, poly(alkylene glycols), alkoxy poly(alkylene glycols), copolymers of methylvinyl ether and maleic acid, urethanes, ethyleneimines, polyurethane-polyether copolymers, and copolymers having units derived from vinyl alcohol, N-vinyl lactams, vinyl pyrrolidone, amides, maleic anhydride, styrenesulfonates, vinylsulfonic acid, vinylsulfonates or 3-hydroxybutyric acid.

21. The method of claim 20, wherein the functionalized acrylates are selected from the group consisting of functionalized copolymers having units derived from acrylic acid, methacrylic acid, 2-hydroxyalkyl acrylate, 2-hydroxyalkylmethacrylate, acrylamides, methacrylamides, epoxy-acrylates.

22. The method of claim 19, wherein in the plurality of functional groups the functional groups are the same.

23. The method of claim 19, wherein in the plurality of functional groups at least one functional group is different from at least one other functional group.

24. The method of claim 19, wherein the carbohydrates comprise monosaccharides, disaccharides, trisaccharides, tetrasaccharides, oligosaccharides or polysaccharides.

25. The method of claim 19, wherein at least two carbohydrates are bonded and each individual carbohydrate is the same.

26. The method of claim 19, wherein at least two carbohydrates are bonded and at least one individual carbohydrate is different from at least one other individual carbohydrate.

27. A composition, comprising:
(a) a paramagnetic bead;
(b) a plurality of hydrophilic copolymer bridges, each bridge being covalently bonded to the paramagnetic bead; and
(c) a plurality of carbohydrates, each carbohydrate being covalently bonded to the same or different hydrophilic copolymer bridge by forming a glycoconjugate with the respective hydrophilic copolymer, wherein each hydrophilic polymer bridge is bonded to the paramagnetic bead via a link formed by an amino group,
wherein the hydrophilic copolymer bridges are formed of functionalized hydrophilic copolymers selected from the group consisting of functionalized acrylates, poly(alkylene glycols), alkoxy poly(alkylene glycols), copolymers of methylvinyl ether and maleic acid, urethanes, ethyleneimines, polyurethane-polyether copolymers, copolymers having units derived from vinyl alcohol, N-vinyl lactams, vinyl pyrrolidone, amides, maleic anhydride, styrenesulfonates, vinylsulfonic acid, vinylsulfonates, N-vinylamides or 3-hydroxybutyric acid, and,
wherein the functionalized acrylates are selected from the group consisting of functionalized copolymers having units derived from acrylic acid, methacrylic acid, 2-hydroxyalkyl acrylate, 2-hydroxyalkylmethacrylate, acrylamides, methacrylamides, epoxy-acrylates, and,
wherein each of the functionalized hydrophilic copolymers includes a plurality of functional groups, comprising:
(a) a first functional group to form a covalent linkage between the magnetic bead and the respective hydrophilic copolymer bridge; and
(b) at least one second functional group, to attach at least one carbohydrate to the hydrophilic copolymer by forming glycoconjugate(s) between the carbohydrate(s) and the hydrophilic copolymer, and
wherein in the plurality of functional groups at least one functional group is different from at least one other functional group.

28. A composition, comprising:
(a) a paramagnetic bead;
(b) a plurality of hydrophilic copolymer bridges, each bridge being covalently bonded to the paramagnetic bead; and
(c) a plurality of carbohydrates, each carbohydrate being covalently bonded to the same or different hydrophilic copolymer bridge by forming a glycoconjugate with the respective hydrophilic copolymer, wherein each hydrophilic polymer bridge is bonded to the paramagnetic bead via a link formed by an amino group,
wherein at least one carbohydrate is different from at least one other carbohydrate.

29. The composition of claim 28, wherein each hydrophilic copolymer is the same.

30. The composition of claim 28, wherein at least one hydrophilic copolymer is different from at least one other hydrophilic copolymer.

31. A composition, comprising:
(a) a paramagnetic bead;
(b) a plurality of hydrophilic copolymer bridges, each bridge being covalently bonded to the paramagnetic bead; and
(c) a plurality of carbohydrates, each carbohydrate being covalently bonded to the same or different hydrophilic copolymer bridge by forming a glycoconjugate with the respective hydrophilic copolymer, wherein each hydrophilic polymer bridge is bonded to the paramagnetic bead via a link formed by an amino group,
wherein each hydrophilic copolymer has the Hildebrand solubility parameter δ of at least about 10 MPa$^{1/2}$.

32. A method for fabricating a paramagnetic bead composition, the method comprising:
(a) immobilizing a plurality of functionalized hydrophilic copolymers on the surface of a paramagnetic bead; and
(b) bonding at least one carbohydrate to each of at least two hydrophilic copolymers, wherein each of the functionalized hydrophilic copolymers includes a plurality of functional groups, comprising a first functional group and at least one second functional group, to thereby obtain the paramagnetic bead composition, wherein the step of bonding comprises reacting the plurality of functionalized hydrophilic copolymers with the carbohydrate(s), wherein at least two glycoconjugates are formed between at least one carbohydrate and the hydrophilic copolymers, wherein in the plurality of functional groups at least one functional group is different from at least one other functional group.

33. A method for fabricating a paramagnetic bead composition, the method comprising:
   (a) immobilizing a plurality of functionalized hydrophilic copolymers on the surface of a paramagnetic bead; and
   (b) bonding at least one carbohydrate to each of at least two hydrophilic copolymers, wherein each of the functionalized hydrophilic copolymers includes a plurality of functional groups, comprising a first functional group and at least one second functional group, to thereby obtain the paramagnetic bead composition, wherein the step of bonding comprises reacting the plurality of functionalized hydrophilic copolymers with the carbohydrate(s), wherein at least two glycoconjugates are formed between at least one carbohydrate and the hydrophilic copolymers, wherein at least two carbohydrates are bonded and at least one individual carbohydrate is different from at least one other individual carbohydrate.

* * * * *